US006042959A

United States Patent [19]
Debe et al.

[11] Patent Number: 6,042,959
[45] Date of Patent: Mar. 28, 2000

[54] MEMBRANE ELECTRODE ASSEMBLY AND METHOD OF ITS MANUFACTURE

[75] Inventors: Mark K. Debe, Stillwater; Thao Ngoc Pham, Minneapolis; Andrew J. Steinbach, St. Paul, all of Minn.

[73] Assignee: 3M Innovative Properties Company, Saint Paul, Minn.

[21] Appl. No.: 08/948,851

[22] Filed: Oct. 10, 1997

[51] Int. Cl.[7] .............................. H01M 8/10; H01M 4/86
[52] U.S. Cl. ................................ 429/33; 429/40; 429/41; 429/42; 204/296; 204/283; 29/623.3
[58] Field of Search .................................. 429/40, 41, 42, 429/33, 623.3; 204/296, 283

[56] References Cited

U.S. PATENT DOCUMENTS

| | | | |
|---|---|---|---|
| 3,442,715 | 5/1969 | Yee et al. | 502/4 |
| 3,676,222 | 7/1972 | Deibert | 429/42 |
| 3,969,545 | 7/1976 | Slocum | 427/163 |
| 4,148,294 | 4/1979 | Scherber et al. | 126/270 |
| 4,155,781 | 5/1979 | Diepers | 148/175 |
| 4,209,008 | 6/1980 | Lemkey et al. | 126/452 |
| 4,215,183 | 7/1980 | MacLeod | 429/30 |
| 4,252,843 | 2/1981 | Dorer et al. | 427/162 |
| 4,252,865 | 2/1981 | Gilbert et al. | 428/611 |
| 4,259,209 | 3/1981 | Nakane et al. | 252/430 |
| 4,340,276 | 7/1982 | Maffitt et al. | 350/164 |
| 4,396,643 | 8/1983 | Kuehn et al. | 427/160 |
| 4,539,256 | 9/1985 | Shipman | 428/315.5 |
| 4,550,123 | 10/1985 | Lopatin et al. | 521/64 |
| 4,557,957 | 12/1985 | Manniso | 428/36 |
| 4,568,598 | 2/1986 | Bilkadi et al. | 428/141 |
| 4,654,281 | 3/1987 | Anderman et al. | 429/209 |
| 4,720,400 | 1/1988 | Manniso | 427/243 |
| 4,726,989 | 2/1988 | Mrozinski | 428/315.5 |
| 4,731,310 | 3/1988 | Anderman et al. | 429/194 |
| 4,735,875 | 4/1988 | Anderman et al. | 429/194 |
| 4,791,037 | 12/1988 | Anderman | 429/196 |
| 4,812,352 | 3/1989 | Debe | 428/142 |
| 4,826,554 | 5/1989 | McIntyre et al. | 156/280 |
| 4,849,311 | 7/1989 | Itoh et al. | 429/192 |

(List continued on next page.)

FOREIGN PATENT DOCUMENTS

| | | |
|---|---|---|
| 1299936 | 5/1992 | Canada . |
| 0 094 679 A2 | 11/1983 | European Pat. Off. . |
| 0 226 911 | 7/1987 | European Pat. Off. . |
| 0 228 602 | 7/1987 | European Pat. Off. . |
| 0 309 259 A2 | 3/1989 | European Pat. Off. . |
| 0 569 062 | 11/1993 | European Pat. Off. . |
| 51-46589 | 4/1976 | Japan . |
| 57-060670 | 4/1982 | Japan . |
| 60-825 | 1/1985 | Japan . |
| 63-117321 | 5/1988 | Japan . |
| 6-68157 | 8/1994 | Japan . |
| 1100497 | 1/1968 | United Kingdom . |
| 1 547 534 | 6/1979 | United Kingdom . |
| WO 94/15210 | 7/1994 | WIPO . |
| WO 95/06002 | 3/1995 | WIPO . |
| WO 97/25369 | 7/1997 | WIPO . |

OTHER PUBLICATIONS

M. Uchida, Y. Aoyama, N. Eda, A. Ohta, J. Electrochem. Soc., New Preparation Method for Polymer–Electrolyte Fuel Cells, vol. 142, No. 2, Feb. 1995.

D. D. DesMarteau, Novel Fluorinated Acids for Phosphoric Acid Fuel Cells, Final Report, Dept. of Chemistry, Clemson University, Clemson, S.C., 1992.

Darryl D. DesMarteau, Novel perfluorinated ionomers and ionenes, Journal of Fluorine Chemistry, 72 (1995) pp. 203–208.

Proceedings from DARPA's Direct Methanol Fuel Cell Program Review, System Planning Corporation, USA Today Bldg., Arlington, VA., Nov. 14–15, 1996, pp. 14–18.

K. Robbie, L.J. Friedrich, S.K. Dew, T. Smy, M.J. Brett, Fabrication of thin films with highly porous microstructures, J. Vac. Sci. Technol. A, vol. 13, No. 3, May/Jun. 1995, pp. 1032–1035.

Kevin Robbie, Michael J. Brett, Akhlesh Laktakia, First thin film realization of a helicoidal bianisotropic medium, J. Vac. Sci. Technol. A 13(6), Nov./Dec. 1995 pp. 2991–2993.

Kenneth G. Kreider, Michael J. Tarlov, James P. Cline, Sputtered thin film pH, electrodes of platinum, palladium, ruthenium, and iridium oxides, Sensprs amd Actiatprs B 29 (1995) pp. 167–172.

E–TEK, Inc., Gas Diffusion Electrodes and Catalyst Materials, C. Noble Metal Catalysts on Carbon, 1995 Catalogue, pp. 15–21.

M. Razaq, A. Bazaag, E. Yeager, Darryl D. DesMarteau, S. Singh, Perfluorosulfonimide as an Additive in Phosphoric Acid Fuel Cell, J. Electrochem. Soc., vol. 136, No. 2, Feb. 1989, pp. 385–390.

M. Razaq, A. Razaaq, E. Yeager, Darryl D. DesMarteau, S. Singh, Oxygen electroreduction in perfluorinated sulphonyl imides, Journal of Applied Electrochemistry 17 (1987) pp. 1057–1064.

Minoru Mizuhata, Kazuaki Yasuda, Keisuke Oguro, Hiroyasu Takenaka, Preparation of Gas Diffusion Electrode with Highly–active Catalyst for PEFCs, Electrochemical Society Proceedings vol. 95–23, pp. 24–33.

Acc. No. 96–005215/01 (Abstract from Derwent Database).
Acc. No. 88–311503/44 (Abstract from Derwent Database).
Acc. No. 88–144518/21 (Abstract from Derwent Database).
Acc. No. 95–218572/29 (Abstract from Derwent Database).
Acc. No. 88–317781/45 (Abstract from Derwent Database).
Acc. No. 95–188591/25 (Abstract from Derwent Database).

*Primary Examiner*—Maria Nuzzolillo
*Assistant Examiner*—Laura Weiner
*Attorney, Agent, or Firm*—Philip Y. Dahl

[57] ABSTRACT

A method is provided for making a membrane electrode that employs a composite membrane, which include both a porous membrane and an ion conducting electrolyte, by partially filling a porous membrane with an ion conducting electrolyte to form a partially filled membrane and then compressing the partially filled membrane with electrode particles so as to remove void volume from the partially filled membrane and embed the electrode particles in the partially filled membrane. The membrane electrode of this invention is suitable for use in electrochemical devices, including proton exchange membrane fuel cells, electrolyzers, chlor-alkali separation membranes, and the like.

14 Claims, 10 Drawing Sheets

U.S. PATENT DOCUMENTS

| | | | |
|---|---|---|---|
| 4,853,305 | 8/1989 | Anderman et al. | 429/212 |
| 4,863,813 | 9/1989 | Kyer | 429/33 |
| 4,867,881 | 9/1989 | Kinzer | 210/490 |
| 4,910,099 | 3/1990 | Gottesfeld | 429/13 |
| 4,957,943 | 9/1990 | McAllister et al. | 521/64 |
| 4,992,126 | 2/1991 | Door | 156/182 |
| 5,039,561 | 8/1991 | Debe | 427/255.6 |
| 5,120,594 | 6/1992 | Mrozinski | 428/195 |
| 5,138,220 | 8/1992 | Kirkpatrick | 213/309 |
| 5,143,805 | 9/1992 | Anderman et al. | 429/217 |
| 5,162,167 | 11/1992 | Minh et al. | 429/30 |
| 5,176,786 | 1/1993 | Debe | 156/600 |
| 5,238,729 | 8/1993 | Debe | 428/245 |
| 5,260,360 | 11/1993 | Mrozinski et al. | 524/95 |
| 5,264,299 | 11/1993 | Krasij et al. | 429/30 |
| 5,277,996 | 1/1994 | Marchetti et al. | 429/44 |
| 5,308,465 | 5/1994 | Hillrichs et al. | 204/283 |
| 5,326,619 | 7/1994 | Dower et al. | 428/164 |
| 5,336,558 | 8/1994 | Debe | 428/323 |
| 5,338,430 | 8/1994 | Parsonage et al. | 204/412 |
| 5,352,651 | 10/1994 | Debe et al. | 503/227 |
| 5,384,208 | 1/1995 | Brand et al. | 429/34 |
| 5,387,462 | 2/1995 | Debe | 428/245 |
| 5,395,705 | 3/1995 | Door et al. | 429/42 |
| 5,399,184 | 3/1995 | Harada | 29/623.4 |
| 5,418,007 | 5/1995 | Debe | 427/154 |
| 5,429,886 | 7/1995 | Struthers | 429/44 |
| 5,459,016 | 10/1995 | Debe et al. | 430/201 |
| 5,460,896 | 10/1995 | Takada et al. | 429/33 |
| 5,472,799 | 12/1995 | Watanabe | 429/30 |
| 5,514,461 | 5/1996 | Meguro et al. | 428/310.5 |
| 5,547,551 | 8/1996 | Bahar et al. | 204/296 |
| 5,599,614 | 2/1997 | Bahar et al. | 442/171 |
| 5,614,306 | 3/1997 | Jobe et al. | 442/381 |
| 5,620,807 | 4/1997 | Mussell et al. | 429/33 |
| 5,626,805 | 5/1997 | Meguro et al. | 264/41 |
| 5,635,039 | 6/1997 | Cisar et al. | 204/252 |
| 5,635,041 | 6/1997 | Bahar et al. | 204/282 |
| 5,641,565 | 6/1997 | Sogo | 428/315.7 |
| 5,645,929 | 7/1997 | Debe | 428/323 |
| 5,659,296 | 8/1997 | Debe et al. | 340/632 |
| 5,702,755 | 12/1997 | Mussell | 427/115 |
| 5,702,839 | 12/1997 | Frost et al. | 429/42 |

MEMBRANE ELECTRODE ASSEMBLY AND METHOD OF ITS MANUFACTURE

FIELD OF THE INVENTION

This invention relates to a process of forming a membrane electrode assembly that comprises a composite membrane and is suitable for use in electrochemical devices, including proton exchange membrane fuel cells, electrolyzers, chlor-alkali separation membranes, sensors, and the like.

BACKGROUND OF THE INVENTION

Electrochemical devices, including proton exchange membrane fuel cells, electrolyzers, chlor-alkali separation membranes, and the like, have been constructed from membrane electrode assemblies (MEAs). Such MEAs comprise one or more electrode portions, which include a catalytic electrode material such as Pt or Pd, in contact with an ion conductive membrane. Ion conductive membranes (ICMs) are used in electrochemical cells as solid electrolytes. In a typical electrochemical cell, an ICM is in contact with cathode and anode electrodes, and transports ions such as protons that are formed at the anode to the cathode, allowing a current of electrons to flow in an external circuit connecting the electrodes.

MEAs are used in hydrogen/oxygen fuel cells. A typical MEA for use in a hydrogen/oxygen fuel cell might comprise a first Pt electrode portion, an ICM comprising a proton-exchange electrolyte, and a second Pt electrode portion. Such an MEA can be used to generate electricity by oxidation of hydrogen gas, as illustrated in the following reactions:

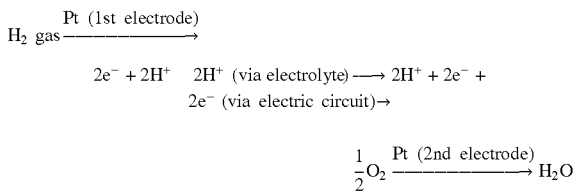

In a typical hydrogen/oxygen fuel cell, the ions to be conducted by the membrane are protons. Importantly, ICMs do not conduct electrons/electricity, since this would render the fuel cell useless, and they must be essentially impermeable to fuel gasses, such as hydrogen and oxygen. Any leakage of the gasses employed in the reaction across the MEA results in waste of the reactants and inefficiency of the cell. For that reason, the ion exchange membrane must have low or no permeability to the gasses employed in the reaction.

ICMs also find use in chlor-alkali cells wherein brine mixtures are separated to form chlorine gas and sodium hydroxide. The membrane selectively transports sodium ions while rejecting chloride ions. ICMs also can be useful for applications such as diffusion dialysis, electrodialysis, and pervaporization and vapor permeation separations. While most ICMs transport cations or protons, membranes that are transportive to anions such as $OH^-$ are known and commercially available.

Commercially-available ICMs are not entirely satisfactory in meeting the performance demands of fuel cells. For example, Nafion™ membranes (DuPont Chemicals, Inc., Wilmington, Del.) which are perfluorocarbon materials having a $SO_3^-$, anion, are inherently weak. Nafion™ membranes are not generally available at thicknesses of less than 50 μm. One reason is that Nafion™ membranes that thin would require reinforcement, thus defeating the purpose of a thin membrane by increasing the overall thickness as well as increasing the electrical resistance of the membrane. While Nafion™ membranes with lower equivalent weight can be used to obtain lower electrical resistance, lower equivalent weight membranes are structurally weaker and still would not obviate the need for reinforcement.

One means of constructing a reinforced membrane is to imbibe or infuse an ion-conductive material into a porous inert reinforcing membrane to make a composite membrane. For example, Gore-Select™ membranes (W. L. Gore & Associates, Inc., Elkton, Md.) comprise a poly (tetrafluoroethylene) (PTFE) membrane having an ion-conductive or ion exchange liquid impregnated therein. U.S. Pat. No. 5,547,551 describes a PTFE membrane fully impregnated with Nafion™ solution for use in fuel cells. Other inert membranes have been mentioned, such as polyolefins and poly(vinylidene fluoride), as suitable carriers for ion-conducting electrolytes.

Composite proton exchange membranes, comprising electrolytes immobilized in porous webs, have been shown to offer superior properties over single component membranes when used in fuel cells. The composite membranes can be made thinner and stronger while giving equivalent conductivity with less electrolyte, and have more dimensional stability even after becoming saturated with water. However, because the membranes employed are initially porous, the gas permeability of the resulting membrane depends in part on the degree to which the membrane is filled by the electrolyte.

These composite membranes are used in fuel cell MEAs that use conventional catalyst electrodes in the form of applied dispersions of either Pt fines or carbon supported Pt catalysts. These conventional catalysts are applied as a coating of ink or paste to either the composite membrane or to an electrode backing layer placed adjacent to the membrane. The ink or paste typically contains electrolyte in the form of an ionomer.

Various structures and means have been used to apply or otherwise bring a catalyst in contact with an electrolyte to form electrodes, e.g., cathodes and anodes. These "membrane electrode assemblies" (MEAs) can include: (a) porous metal films or planar distributions of metal particles or carbon supported catalyst powders deposited on the surface of the ICM; (b) metal grids or meshes deposited on or imbedded in the ICM; or (c) catalytically active nanostructured composite elements embedded in the, surface of the ICM.

Nanostructured composite articles have been disclosed. See, for example, U.S. Pat. Nos. 4,812,352, 5,039,561, 5,176,786, 5,336,558, 5,338,430, and 5,238,729. U.S. Pat. No. 5,338,430 discloses that nanostructured electrodes embedded in solid polymer electrolyte offer superior properties over conventional electrodes employing metal fines or carbon supported metal catalysts, including: protection of the embedded electrode material, more efficient use of the electrode material, and enhanced catalytic activity.

SUMMARY OF THE INVENTION

Briefly, this invention provides a method of making a membrane electrode assembly that comprises a composite membrane, which includes both a porous membrane and an ion conducting electrolyte, by partially filling a porous membrane with an ion conducting electrolyte to form a partially filled membrane and then compressing together the partially filled membrane and electrode particles so as to remove void volume from the partially filled membrane and embed the electrode particles in the partially filled membrane. The membrane electrode assembly of this invention is suitable for use in electrochemical devices, including proton exchange membrane fuel cells, electrolyzers, chlor-alkali separation membranes, sensors and the like.

In another aspect, the present invention provides a composite membrane including a polymerization product comprising one or more monomers having the formula $CH_2=CH-Ar-SO_2-N^--SO_2(C_{1+n}F_{3+2n})$, wherein n is 0–11, preferably 0–3, and most preferably 0, and wherein Ar is any substituted or unsubstituted aryl group, preferably of molecular weight less than 400 and most preferably a divalent phenyl group.

In a further aspect, the invention provides a fuel cell assembly comprising at least one membrane electrode assembly disclosed above.

In yet another aspect, the invention provides an electrochemical device comprising at least one MEA disclosed above.

In the method of the present invention, a porous membrane is partially filled with an ion conducting electrolyte to form a partially filled membrane. The partially filled membrane is then pressed with electrode particles so as to embed the electrode particles in the partially filled membrane. It was found that this pressing step also removed void volume remaining after the filling step, and therefore resulted in a thinner and less porous composite membrane than previously contemplated. In a preferred embodiment, the present invention provides a method for forming a membrane electrode assembly that comprises embedded electrode particles, which may be nanostructured catalyst particles, together with a composite membrane.

Furthermore, under certain circumstances it was observed that, not only was the void space of the porous membrane filled, but the porous structure itself was obliterated. Under a scanning electron microscope the resulting membrane appeared uniform, ever at a magnification of 10,000×. Thus, in another preferred embodiment, the present invention provides a method for forming a membrane electrode assembly that comprises a composite membrane which has acquired a uniform, undifferentiated structure, that is, wherein the porous structure of the initially porous membrane is obliterated.

In addition, resulting MEA's were shown to function well in electrochemical cells.

In this application:

"composite membrane" means a membrane composed of more than one material and including both a porous membrane material and an ion conducting electrolyte material;

"membrane electrode assembly" means a structure comprising a membrane that includes an electrolyte and at least one but preferably two or more electrodes adjoining the membrane;

"substituted" means, for a chemical species, having a conventional substituent that does not interfere with the desired product;

"nanostructured element" means an acicular, discrete, sub-microscopic structure comprising an electrically conductive material on at least a portion of its surface;

"acicular" means having a ratio of length to average cross-sectional width of greater than or equal to 3;

"discrete" refers to distinct elements, having a separate identity, but does not preclude elements from being in contact with one another;

"sub-microscopic" means having at least one dimension smaller than about a micrometer;

"Gurley number" means a measure of the resistance to gas flow of a membrane, expressed as the time necessary for a given volume of gas to pass through a standard area of the membrane under standard conditions, as specified in ASTMD726-58, Method A, described further below; and "pore size" means a measure of size of the largest pore in a membrane as specified in ASTM F-316-80, described further below.

It is an advantage of the present invention to provide a method of making a strong, thin, and more gas impervious membrane electrode for use in membrane electrode assemblies. In particular, it is an advantage of the present invention to provide a method of making a membrane electrode comprising a thinner and more completely filled composite membrane with nanostructured electrodes. In addition, it is an advantage of the present invention to provide a method of making a membrane electrode comprising a thin and non-porous composite membrane lacking any visible porous structure and having nanostructured electrodes.

DETAILED DESCRIPTION OF THE PREFERRED EMBODIMENTS

In the method of the present invention, a porous membrane is partially filled with an ion conducting electrolyte to form a partially filled composite membrane. The partially filled membrane is then compressed with electrode particles so as to further exclude void volume from the membrane and embed the electrode particles in the membrane.

Any suitable porous membrane may be used. Porous membranes useful as reinforcing membranes of the invention can be of any construction having sufficient porosity to allow at least one solidifiable ICM to be infused or imbibed thereinto and having sufficient strength to withstand operating conditions in an electrochemical cell. Preferably, porous membranes useful in the invention comprise a polymer that is inert to conditions in the cell, such as a polyolefin, or a halogenated, preferably fluorinated, poly(vinyl) resin. Expanded PTFE membranes may be used, such as Poreflon™, produced by Sumitomo Electric Industries, Inc., Tokyo, Japan, and Tetratex™. produced by Tetratec, Inc., Feasterville, Pa.

Figure 3:
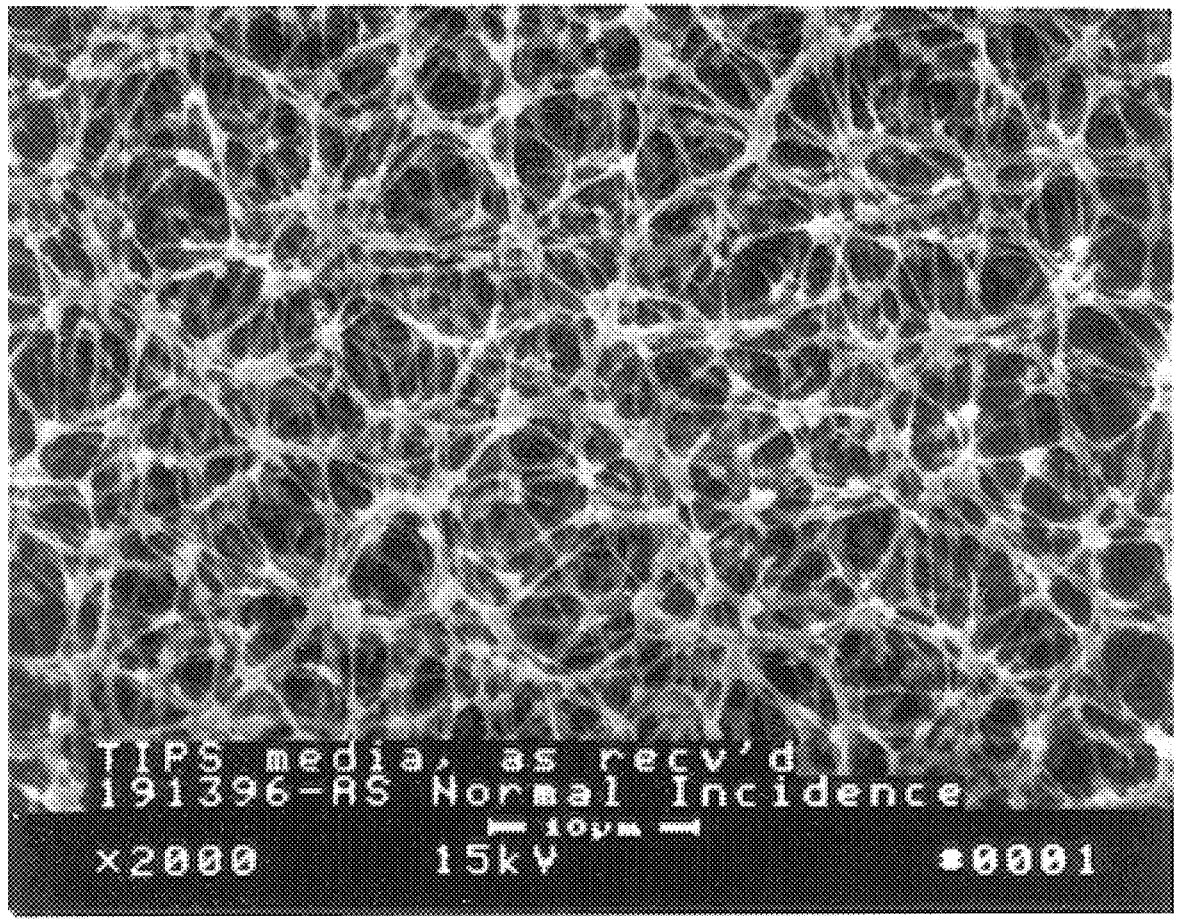
FIG. 3 is a scanning electron micrograph taken at 2,000× magnification of the surface of a membrane useful in the method of the present invention.
Figure 9:
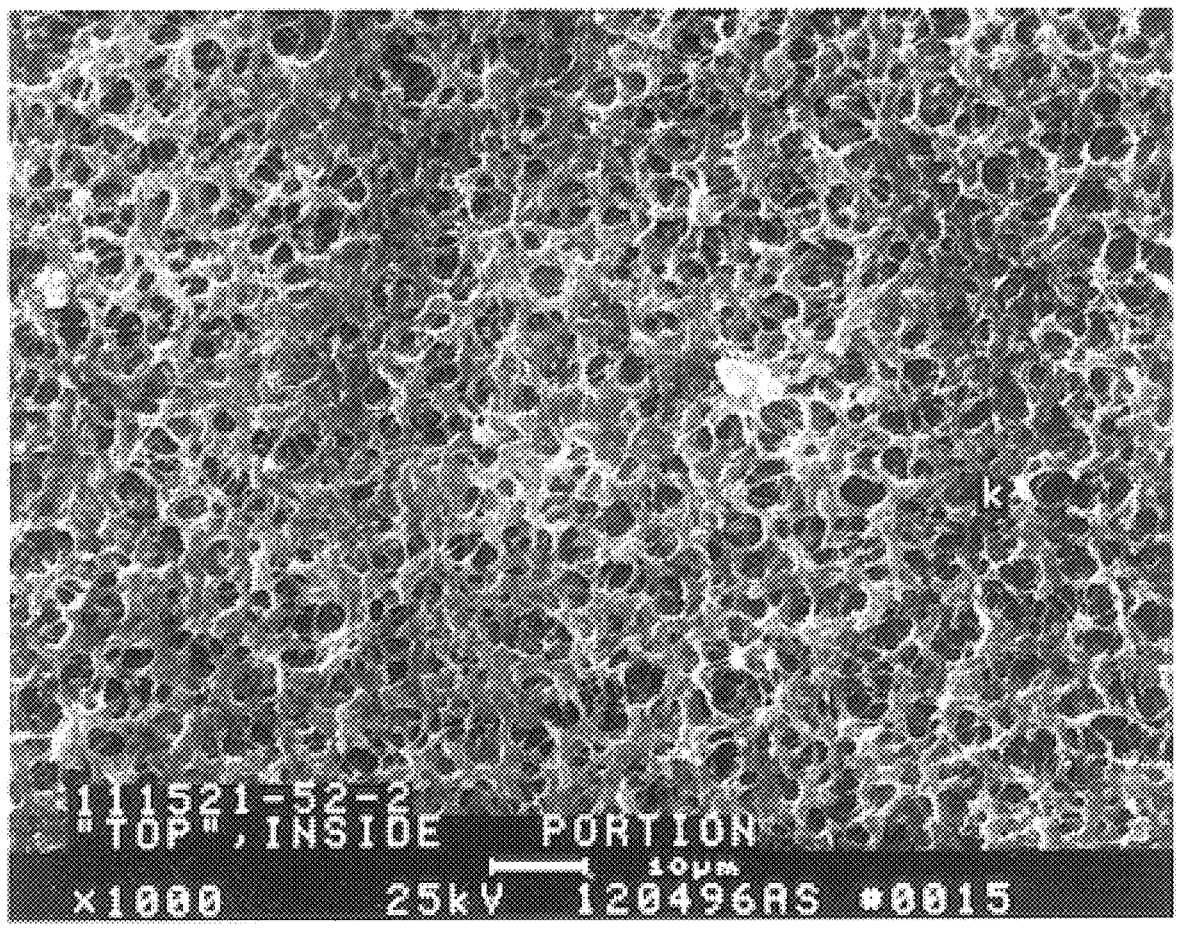
FIG. 9 is a scanning electron micrograph taken at 1,000× magnification of the surface of a membrane useful in the method of the present invention.

More preferably, porous membranes of the invention comprise microporous films prepared by thermally-induced phase separation (TIPS) methods, as described in, e.g., U.S. Pat. Nos. 4,539,256, 4,726,989, 4,867,881, 5,120,594 and 5,260,360, the teachings of which are incorporated herein by reference. TIPS films exhibit a multiplicity of spaced, randomly dispersed, equiaxed, nonuniform shaped particles of a thermoplastic polymer in the form of a film, membrane, or sheet material. Micropores defined by the particles preferably are of sufficient size to allow ICMs to be incorporated therein. FIGS. 3 and 9 are scanning electron micrographs at 2000× and 1000× magnification, respectively, of the porous surfaces of two such TIPS membranes.

Polymers suitable for preparing films by the TIPS process include thermoplastic polymers, thermosensitive polymers, and mixtures of these polymers, so long as the mixed polymers are compatible. Thermosensitive polymers such as ultrahigh molecular weight polyethylene (UHMWPE) cannot be melt-processed directly but can be melt-processed in the presence of a diluent that lowers the viscosity thereof sufficiently for melt processing.

Suitable polymers include, for example, crystallizable vinyl polymers, condensation polymers, and oxidation polymers. Representative crystallizable vinyl polymers include, for example, high- and low-density polyethylene, polypropylene, polybutadiene, polyacrylates such as poly (methyl methacrylate), fluorine-containing polymers such as poly(vinylidene fluoride), and the like. Useful condensation polymers include, for example, polyesters, such as poly (ethylene terephthalate) and poly(butylene terephthalate), polyamides, including many members of the Nylon™ family, polycarbonates, and polysulfones. Useful oxidation polymers include, for example, poly(phenylene oxide) and poly(ether ketone). Blends of polymers and copolymers may also be useful in the invention. Preferred polymers for use as reinforcing membranes of the invention include crystallizable polymers, such as polyolefins and fluorine-containing polymers, because of their resistance to hydrolysis and oxidation. Preferred polyolefins include high density polyethylene, polypropylene, ethylene-propylene copolymers, and poly(vinylidene fluoride).

Any suitable ion exchange electrolyte may be used. The electrolytes are preferably solids or gels, under the operating conditions of the electrochemical cell. Electrolytes useful in the present invention can include ion conductive materials, such as polymer electrolytes, and ion-exchange resins. The electrolytes are preferably proton conducting ionomers suitable for use in proton exchange membrane fuel cells.

Ion conductive materials useful in the invention can be complexes of an alkalai metal or alkalai earth metal salt or a protonic acid with one or more polar polymers such as a polyether, polyester, or polyimide, or complexes of an alkalai metal or alkalai earth metal salt or a protonic acid with a network or crosslinked polymer containing the above polar polymer as a segment. Useful polyethers include: polyoxyalkylenes, such as polyethylene glycol, polyethylene glycol monoether, polyethylene glycol diether, polypropylene glycol, polypropylene glycol monoether, and polypropylene glycol diether; copolymers of these polyethers, such as poly(oxyethylene-co-oxypropylene) glycol, poly(oxyethylene-co-oxypropylene) glycol monoether, and poly(oxyethylene-co-oxypropylene) glycol diether; condensation products of ethylenediamine with the above polyoxyalkylenes; esters, such as phosphoric acid esters, aliphatic carboxylic acid esters or aromatic carboxylic acid esters of the above polyoxyalkylenes. Copolymers of, e.g., polyethylene glycol with dialky siloxanes, polyethylene glycol with maleic anhydride, or polyethylene glycol monoethyl ether with methacrylic acid are known in the art to exhibit sufficient ionic conductivity to be useful in an ICM of the invention. Useful complex-forming reagents can include alkalai metal salts, alkalai metal earth salts, and protonic acids and protonic acid salts. Counterions useful in the above salts can be halogen ion, perchloric ion, thiocyanate ion, trifluoromethane sulfonic ion, borofluoric ion, and the like. Representative examples of such salts include, but are not limited to, lithium fluoride, sodium iodide, lithium iodide, lithium perchlorate, sodium thiocyanate, lithium trifluoromethane sulfonate, lithium borofluoride, lithium hexafluorophosphate, phosphoric acid, sulfuric acid, trifluoromethane sulfonic acid, tetrafluoroethylene sulfonic acid, hexafluorobutane sulfonic acid, and the like.

Ion-exchange resins useful as electrolytes in the present invention include hydrocarbon- and fluorocarbon-type resins. Hydrocarbon-type ion-exchange resins can include phenolic or sulfonic acid-type resins; condensation resins such as phenol-formaldehyde, polystyrene, styrene-divinyl benzene copolymers, styrene-butadiene copolymers, styrene-divinylbenzene-vinylchloride terpolymers, and the like, that are imbued with cation-exchange ability by sulfonation, or are imbued with anion-exchange ability by chloromethylation followed by conversion to the corresponding quaternary amine.

Fluorocarbon-type ion-exchange resins can include hydrates of a tetrafluoroethylene-perfluorosulfonyl ethoxyvinyl ether or tetrafluoroethylene-hydroxylated (perfluoro vinyl ether) copolymers. When oxidation and/or acid resistance is desirable, for instance, at the cathode of a fuel cell, fluorocarbon-type resins having sulfonic, carboxylic and/or phosphoric acid functionality are preferred. Fluorocarbon-type resins typically exhibit excellent resistance to oxidation by halogen, strong acids and bases, and can be preferable for composite electrolyte membranes useful in the invention. One family of fluorocarbon-type resins having sulfonic acid group functionality is the Nafion™ resins (DuPont Chemicals, Wilmington, Del., available from ElectroChem, Inc., Woburn, Mass., and Aldrich Chemical Co., Inc., Milwaukee, Wis.). Other fluorocarbon-type ion-exchange resins that can be useful in the invention comprise (co) polymers of olefins containing aryl perfluoroalkyl sulfonylimide cation-exchange groups, having the general formula (I): $CH_2=CH-Ar-SO_2-N^--SO_2(C_{1+n}F_{3+2n})$, wherein n is 0–11, preferably 0–3, and most preferably 0, and wherein Ar is any substituted or unsubstituted aryl group, preferably monocyclic and most preferably a divalent phenyl group, referred to as phenyl herein. Ar may include any substituted or unsubstituted aromatic moieties, including benzene, naphthalene, anthracene, phenanthrene, indene, fluorene, cyclopentadiene and pyrene, wherein the moieties are preferably molecular weight 400 or less and more preferably 100 or less. One such resin is p-STSI, an ion conductive material derived from free radical polymerization of styrenyl trifluoromethyl sulfonylimide (STSI) having the formula (II): styrenyl-$SO_2N^-$—$SO_2CF_3$. This embodiment, wherein n=0 and Ar is unsubstituted phenyl, is the most preferred embodiment according to formula I.

Preferably the electrolyte is a polymeric resin. In one embodiment the most preferred electrolyte is Nafion™. In another embodiment, wherein the porous structure of the composite membrane is obliterated, the preferred electrolytes are polyolefins containing aryl perfluoroalkyl sulfonylimide groups according to formula (I), above, and the most preferred electrolyte is p-STSI.

Any suitable procedure may be used to partially fill the porous membrane with the electrolyte. In the "multiple dipping" approach, illustrated in the Examples, the porous membrane is immersed in relatively low concentration electrolyte solution for short times, dried, and the process repeated multiple times. The dipping may be repeated until the weight of the membrane approaches a steady state as no further electrolyte is incorporated. Preferably, the dipping is repeated until at least this point, but may be terminated before this point. Any concentration of electrolyte solution may be used, however, very low concentrations may require increased dipping repetitions or may result in lower loading of electrolyte. A solution of about 5 wt % is preferred. The membrane may be dried by any means, preferably at elevated temperature such as in an air oven. Drying temperature is preferably between 40° C. and 60° C. Without being limited to any one theory, it is proposed that the adsorption of the electrolyte polymer onto the porous matrix fibrils occurs primarily as the concentration of the solution increases during the solvent evaporation stage, so increasing the number of such events will enhance filling.

In the "long soak" approach, illustrated in the Examples, the porous membrane is immersed in the electrolyte solution for prolonged periods, preferably exceeding 20 minutes, then dried. Any concentration of electrolyte solution may be used, however, very low concentrations may require increased soaking time or may result in lower loading of electrolyte. A solution of about 5 wt % is preferred. The membrane may be dried by any means, preferably at elevated temperature such as in an air oven. Drying temperature is preferably between 40° C. and 60° C.

In the "vacuum" approach, illustrated in the Examples, sub-atmospheric air pressure is applied to the underside of the porous membrane by any suitable means to draw an electrolyte solution applied to its top through the membrane and the membrane is then dried. A Venturi pump may be used to generate sub-atmospheric air pressure. The vacuum is applied for as long as necessary to draw enough solution into the membrane so as to partially fill the membrane, preferably between 1 second and 10 minutes. Any concentration of electrolyte solution may be used, however, higher concentrations appear to result in increased loading of electrolyte, and higher viscosity requires increased time to load the solution into the membrane. A solution of greater than about 10 wt % is preferred, and a solution of about 20 wt % is most preferred. The membrane may be dried by any means, preferably at elevated temperature such as in an air oven. Drying temperature is preferably between 40° C. and 60° C.

In the "hydraulic press" approach, illustrated in the Examples, a room temperature mechanical press is used to force high concentration viscous electrolyte solutions through the porous membrane. Preferably, the membrane material is sandwiched between impermeable film layers having mask holes cut in the area to be filled with electrolyte. The mask layers may be prepared from polyethylene terephthalate (PET) film, preferably about 100 micrometers thick. The electrolyte solution is added dropwise to the membrane surface. Additional layers or shims may be added before the membrane is placed in the press. The pressure used may be up to 2 tons/$cm^2$, preferably between 0.1–1.0 tons/$cm^2$, and more preferably 0.4–0.6 tons/$cm^2$. Any means of applying pressure may be employed, including nip rollers and flat bed presses. A continuous process is preferred. Force is applied for as long as necessary to partially fill the membrane, typically between 1 second and 10 minutes. After pressing, any excess solution is wiped off the surface of the membrane and the membrane is dried. The membrane may be dried by any means, preferably at elevated temperature such as in an air oven. Drying temperature is preferably between 40° C. and 60° C.

In the "evaporation" approach the porous membrane is placed over a thin volume of solution, causing the solution to partially fill the membrane from the underside by capillarity. The solvent is allowed to evaporate through the top surface of the membrane. The process may be carried out at any temperature at which the solvent will evaporate, preferably room temperature or higher.

Preferably, the hydraulic press, vacuum or multiple dipping method is used. Most preferably, the hydraulic press method is used.

The amount of electrolyte solution used in the filling process should be sufficient to achieve the degree of filling desired but is preferably in excess of that which would theoretically fill the membrane. The amount of electrolyte imbibed in the pores or adsorbed on the fibrils of the membrane after the partial filling should be sufficient to fill between 10% and 90% of the available pore volume. Preferably, more than 15% of the available pore volume is filled. Most preferably, between 35% and 65% of the available pore volume is filled. The electrolyte may be present as a coating on the structural fibrils of the porous membrane or it may wet out the membrane, filling the entire cross section of some pores. The increase in density of the membrane after partial filling should be at least 0.01 g/$cm^3$ but is preferably at least 0.1 g/$cm^3$ but less than 1.2 g/$cm^3$.

Any suitable electrode particles may be used. At least a portion of the surface of suitable electrode particles is composed of a catalytic material. Preferably, nanostructured elements are used, as described below. However, other electrode particles may be used, including metal fines or metal-coated support particles such as carbon particles. The catalytic material should be appropriate to the intended use of the MEA. Preferably the catalytic material is a Group VII metal or an alloy thereof and most preferably Pt or an alloy thereof.

Nanostructured elements suitable for use in the present invention may comprise metal-coated whiskers of organic pigment, most preferably C.I. PIGMENT RED 149 (perylene red). The crystalline whiskers have substantially uniform but not identical cross-sections, and high length-to-width ratios. The nanostructured whiskers are conformally coated with materials suitable for catalysis, and which endow the whiskers with a fine nanoscopic surface structure capable of acting as multiple catalytic sites.

U.S. Pat. Nos. 4,812,352 and 5,039,561 disclose a preferred method for making an organic-based microstructured layer of whiskers, suitable for coating with a nanoscopic surface layer to generate nanostructured whiskers suitable for use in the present invention. The disclosures of U.S. Pat. Nos. 4,812,352 and 5,039,561 are incorporated herein by reference. As disclosed therein, a method for making a microstructured layer of whiskers comprises the steps of i) depositing or condensing a vapor of an organic material as a thin, continuous or discontinuous layer onto a substrate; and ii) annealing the deposited organic layer in a vacuum for a time and at a temperature sufficient to induce a physical change in the deposited organic layer to form a microstructured layer comprising a dense array of discrete microstructures or whiskers but insufficient to cause the organic layer to evaporate or sublime.

A layer of whiskers can be deposited on a substrate of any desired size by a totally dry process, and conveniently and rapidly patterned using, for example, high resolution (dry) laser ablation means.

Orientation of the whiskers is generally uniform in relation to the surface of the substrate. The whiskers are usually oriented normal to the original substrate surface, the surface normal direction being defined as that direction of the line perpendicular to an imaginary plane lying tangent to the local substrate surface at the point of contact of the base of the whisker with the substrate surface. The surface normal direction is seen to follow the contours of the surface of the substrate. The major axes of the whiskers can be parallel or nonparallel to each other.

Alternatively, the whiskers can be nonuniform in shape, size, and orientation. For example, the tops of the whiskers can be bent, curled, or curved, or the whiskers can be bent, curled, or curved over their entire length.

Preferably, the whiskers are of uniform length and shape, and have uniform cross-sectional dimensions along their major axes. The preferred length of each whisker is less than about 50 micrometers. More preferably, the length of each whisker is in the range from about 0.1 to 5 micrometers, most preferably 0.1 to 3 micrometers. Within any whisker layer it is preferable that the whiskers be of uniform length. Preferably, the average cross-sectional dimension of each whisker is less than about 1 micrometer, more preferably 0.01 to 0.5 micrometer. Most preferably, the average cross-sectional dimension of each whisker is in the range from 0.03 to 0.3 micrometer.

Preferably, the whiskers have an areal number density in the range from about $10^7$ to about $10^{11}$ whiskers per square centimeter. More preferably, the whiskers have an areal density in the range from about $10^8$ to about $10^{10}$ whiskers per square centimeter.

The whiskers can have a variety of orientations and straight and curved shapes. Any one layer can comprise a combination of orientations and shapes. The whiskers have an aspect ratio (i.e., a length to diameter ratio) preferably in the range of from about 3:1 to about 100:1.

Materials useful as a substrate include those which maintain their integrity at the temperature and vacuum imposed upon them during the vapor deposition and annealing steps. The substrate can be flexible or rigid, planar or non-planar, convex, concave, textured, or combinations thereof. Preferred substrate materials include organic materials and inorganic materials (including, for example, glasses, ceramics, metals, and semiconductors). The preferred inorganic substrate material is glass or metal. The preferred organic substrate material is a polyimide. Representative organic substrates include those that are stable at the annealing temperature, for example, polymers such as polyimide film (commercially available, for example, under the trade designation "KAPTON" from DuPont Electronics, Wilmington, Del.), high temperature stable polyimides, polyesters, polyamids, and polyaramids. Metals useful as substrates include, for example, aluminum, cobalt, copper, molybdenum, nickel, platinum, tantalum, or combination thereof Ceramics useful as a substrate material include, for example, metal or non-metal oxides such as alumina and silica. A useful inorganic nonmetal is silicon.

The organic material from which the whiskers can be formed may be coated onto the substrate using techniques known in the art for applying a layer of an organic material onto a substrate, including, for example, vapor phase deposition (e.g., vacuum evaporation, sublimation, and chemical vapor deposition), and solution coating or dispersion coating (e.g., dip coating, spray coating, spin coating, blade or knife coating, bar coating, roll coating, and pour coating (i.e., pouring a liquid onto a surface and allowing the liquid to flow over the surface)). Preferably, the organic layer is applied by physical vacuum vapor deposition (i.e., sublimation of the organic material under an applied vacuum).

Useful organic materials for producing whiskers by, for example, coating followed by plasma etching, can include for example, polymers and prepolymers thereof (e.g., thermoplastic polymers such as, for example, alkyds, melamines, urea formaldehydes, diallyl phthalates, epoxies, phenolics, polyesters, and silicones; thermoset polymers, such as acrylonitrile-butadiene-styrenes, acetals, acrylics, cellulosics, chlorinated polyethers, ethylene-vinyl acetates, fluorocarbons, ionomers, nylons, parylenes, phenoxies, polyallomers, polyethylenes, polypropylenes, polyamide-imides, polyimides, polycarbonates, polyesters, polyphenylene oxides, polystyrenes, polysulfones, and vinyls); and organometallics (e.g., bis($\eta^5$-cyclopentadienyl)iron (II), iron pentacarbonyl, ruthenium pentacarbonyl, osmium pentacarbonyl, chromium hexacarbonyl, molybdenum hexacarbonyl, tungsten hexacarbonyl, and tris (triphenylphosphine) rhodium chloride).

Preferably, the chemical composition of the organic-based whisker layer will be the same as that of the starting organic material. Preferred organic materials useful in preparing the whisker layer include, for example, planar molecules comprising chains or rings over which π-electron density is extensively delocalized. These organic materials generally crystallize in a herringbone configuration. Preferred organic materials can be broadly classified as polynuclear aromatic hydrocarbons and heterocyclic aromatic compounds.

Polynuclear aromatic hydrocarbons are described in Morrison and Boyd, *Organic Chemistry*, Third Edition, Allyn and Bacon, Inc. (Boston: 1974), Chapter 30. Heterocyclic aromatic compounds are described in Morrison and Boyd, supra, Chapter 31.

Preferred polynuclear aromatic hydrocarbons, which are commercially available, include, for example, naphthalenes, phenanthrenes, perylenes, anthracenes, coronenes, and pyrenes. A preferred polynuclear aromatic hydrocarbon is N,N'-di(3,5-xylyl)perylene-3,4,9,10 bis(dicarboximide) (commercially available under the trade designation "C. I. PIGMENT RED 149" from American Hoechst Corp. of Somerset, N.J.), herein designated "perylene red."

Preferred heterocyclic aromatic compounds, which are commercially available, include, for example, phthalocyanines, porphyrins, carbazoles, purines, and pterins. Representative examples of heterocyclic aromatic compounds include, for example, metal-free phthalocyanine (e.g., dihydrogen phthalocyanine) and its metal complexes (e.g. copper phthalocyanine).

The organic materials preferably are capable of forming a continuous layer when deposited onto a substrate. Preferably, the thickness of this continuous layer is in the range from 1 nanometer to about one thousand nanometers.

Orientation of the whiskers can be affected by the substrate temperature, the deposition rate, and angle of incidence during deposition of the organic layer. If the temperature of the substrate during deposition of the organic material is sufficiently high (i.e., above a critical substrate temperature which has been associated in the art with a value one-third the boiling point (K) of the organic material), the deposited organic material will form randomly oriented whiskers either as deposited or when subsequently annealed. If the temperature of the substrate during deposition is relatively low (i.e., below the critical substrate temperature), the deposited organic material tends to form uniformly oriented whiskers when annealed. For example, if uniformly oriented whiskers comprising perylene red are desired, the temperature of the substrate during the deposition of the perylene red is preferably about 0 to about 30° C. Certain subsequent conformal coating processes, such as DC magnetron sputtering and cathodic arc vacuum processes, can produce curvilinear whiskers.

There can be an optimum maximum annealing temperature for different film thicknesses in order to fully convert the deposited layer to whiskers. When fully converted, the major dimension of each whisker is directly proportional to the thickness of the initially deposited organic layer. Since the whiskers are discrete, are separated by distances on the order of their cross-sectional dimensions, and preferably have uniform cross-sectional dimensions, and all the original organic film material is converted to whiskers, conservation of mass implies that the lengths of the whiskers will be proportional to the thickness of the layer initially deposited. Due to this relationship of the original organic layer thickness to the lengths of the whiskers, and the independence of cross-sectional dimensions from length, the lengths and aspect ratios of the whiskers can be varied independently of their cross-sectional dimensions and areal densities. For example, it has been found that the length of whiskers are approximately 10–15 times the thickness of the vapor deposited perylene red layer, when the thickness ranges from about 0.05 to about 0.2 micrometer. The surface area of the whisker layer (i.e., the sum of the surface areas of the individual whiskers) is much greater than that of the organic layer initially deposited on the substrate. Preferably, thickness of the initially deposited layer is in the range from about 0.03 to about 0.25 micrometer.

Each individual whisker can be monocrystalline or polycrystalline, rather than amorphous. The whisker layer can have highly anisotropic properties due to the crystalline nature and uniform orientation of the whiskers.

If a discontinuous distribution of whiskers is desired, masks may be used in the organic layer deposition step to selectively coat specific areas or regions of the substrate. Other techniques known in the art for selectively depositing an organic layer on specific areas or regions of a substrate may also be useful.

In the annealing step, the substrate having an organic layer coated thereon is heated in a vacuum for a time and at a temperature sufficient for the coated organic layer to undergo a physical change, wherein the organic layer grows to form a whisker layer comprising a dense array of discrete, oriented monocrystalline or polycrystalline whiskers. Uniform orientation of the whiskers is an inherent consequence of the annealing process when the substrate temperature during deposition is sufficiently low. Exposure of the coated substrate to the atmosphere prior to the annealing step is not observed to be detrimental to subsequent whisker formation.

If, for example, the coated organic material is perylene red or copper phthalocyanine, annealing is preferably done in a vacuum (i.e., less than about 0.13 Pa) at a temperature in the range from about 160 to about 270° C. The annealing time necessary to convert the original organic layer to the whisker layer is dependent on the annealing temperature. Typically, an annealing time in the range from about 10 minutes to about 6 hours is sufficient. Preferably the annealing time is in the range from about 20 minutes to about 4 hours. Further, for perylene red, the optimum annealing temperature to convert all of the original organic layer to a whisker layer, but not sublime it away, is observed to vary with the deposited layer thickness. Typically, for original organic layer thicknesses of 0.05 to 0.15 micrometer, the temperature is in the range of 245 to 270° C.

The time interval between the vapor deposition step and the annealing step can vary from several minutes to several months, with no significant adverse effect, provided the coated composite is stored in a covered container to minimize contamination (e.g., dust). As the whiskers grow, the organic infrared band intensities change and the laser specular reflectivity drops, allowing the conversion to be carefully monitored, for example, in situ by surface infrared spectroscopy. After the whiskers have grown to the desired dimensions, the resulting layered structure, which comprises the substrate and the whiskers, is allowed to cool before being brought to atmospheric pressure.

If a patterned distribution of whiskers is desired, whiskers may be selectively removed from the substrate, for example, by mechanical means, vacuum process means, chemical means, gas pressure or fluid means, radiation means, and combinations thereof. Useful mechanical means include, for example, scraping whiskers off the substrate with a sharp instrument (e.g., with a razor blade), and encapsulating with a polymer followed by delamination. Useful radiation means include laser or light ablation. Such ablation can result in a patterned electrode. Useful chemical means include, for example, acid etching selected areas or regions of the whisker layer. Useful vacuum means include, for example, ion sputtering and reactive ion etching. Useful air pressure means include, for example, blowing the whiskers off the substrate, with a gas (e.g., air) or fluid stream. Combinations of the above are also possible, such as use of photoresists and photolithography.

The whiskers can be extensions of the substrate and of the same material as the substrate by, e.g., vapor depositing a discontinuous metal microisland mask onto the surface of a polymer, then plasma or reactive ion etching away the polymer material not masked by the metal microislands, to leave polymer substrate posts protruding from the surface, so long as they are transferable to the ICM.

Other methods for making microstructured layers of whiskers or nanostructured elements are known in the art. For example, methods for making organic microstructured layers of whiskers are disclosed in *Materials Science and Engineering*, A158 (1992), pp. 1–6; *J. Vac. Sci. Technol. A*, 5, (4), July/August, 1987, pp. 1914–16; *J. Vac. Sci. Technol. A*, 6, (3), May/August, 1988, pp. 1907–11; *Thin Solid Films*, 186, 1990, pp. 327–47; *J. Mat. Sci.*, 25, 1990, pp. 5257–68; *Rapidly Quenched Metals*, Proc. of the Fifth Int. Conf. on Rapidly Quenched Metals, Wurzburg, Germany (Sep. 3–7, 1984), S. Steeb et al., eds., Elsevier Science Publishers B. V., New York, (1985), pp. 1117–24; *Photo. Sci. and Eng.*, 24, (4), July/August, 1980, pp. 211–16; and U.S. Pat. Nos. 4,568,598 and 4,340,276, the disclosures of which patents are incorporated herein by reference. Methods for making inorganic-based microstructured layers of whiskers are disclosed, for example, in *J. Vac. Sci. Tech. A*, 1, (3), July/September, 1983, pp. 1398–1402 and U.S. Pat. No. 3,969,545; U.S. Pat. Nos. 4,252,865, 4,396,643, 4,148,294, 4,252,843, 4,155,781, 4,209,008, and 5,138,220, the disclosures of which patents are incorporated herein by reference.

Useful inorganic materials for producing whiskers include, for example, carbon, diamond-like carbon, ceramics (e.g., metal or non-metal oxides such as alumina, silica, iron oxide, and copper oxide; metal or non-metal nitrides such as silicon nitride and titanium nitride; and metal or non-metal carbides such as silicon carbide; metal or non-metal borides such as titanium boride); metal or non-metal sulfides such as cadmium sulfide and zinc sulfide; metal silicides such as magnesium silicide, calcium suicide, and iron suicide; metals (e.g., noble metals such as gold, silver, platinum, osmium, iridium, palladium, ruthenium, rhodium, and combinations thereof; transition metals such as scandium, vanadium, chromium, manganese, cobalt, nickel, copper, zirconium, and combinations thereof; low melting metals such as bismuth, lead, indium, antimony, tin, zinc, and aluminum; refractory metals such as tungsten, rhenium, tantalum, molybdenum, and combinations thereof); and semiconductor materials (e.g., diamond, germanium, selenium, arsenic, silicon, tellurium, gallium arsenide, gallium antimonide, gallium phosphide, aluminum antimonide, indium antimonide, indium tin oxide, zinc antimonide, indium phosphide, aluminum gallium arsenide, zinc telluride, and combinations thereof).

The whiskers of the preferred embodiment can be made to have random orientations by control of the substrate temperature during the deposition of the initial PR149 layer, as described above. They can also be made to have curvilinear shapes by conditions of the conformal coating process. As discussed in FIG. 6 of L. Aleksandrov, "GROWTH OF CRYSTALLINE SEMICONDUCTOR MATERIALS ON CRYSTAL SURFACES," Chapter 1, Elsevier, New York, 1984, the energies of the arriving atoms applied by different coating methods, e.g., thermal evaporation deposition, ion deposition, sputtering and implantation, can range over 5 orders of magnitude.

It is within the scope of the present invention to modify the methods for making a microstructured layer of whiskers to make a discontinuous distribution of whiskers.

Preferably, the one or more layers of conformal coating material, if applied, serve as a functional layer imparting desirable catalytic properties, as well as electrical conductivity and mechanical properties (e.g., strengthens and/or protects the whiskers comprising the whisker layer), and low vapor pressure properties.

The conformal coating material preferably can be an inorganic material or it can be an organic material including a polymeric material. Useful inorganic conformal coating materials include, for example, those described above in the description of the whiskers. Useful organic materials include, for example, conductive polymers (e.g., polyacetylene), polymers derived from poly-p-xylylene, and materials capable of forming self-assembled layers.

The preferred thickness of the conformal coating is typically in the range from about 0.2 to about 50 nm. The conformal coating may be deposited onto the whisker layer using conventional techniques, including, for example, those disclosed in U.S. Pat. Nos. 4,812,352 and 5,039,561, the disclosures of which are incorporated herein by reference. Any method that avoids disturbance of the whiskers by mechanical forces can be used to deposit the conformal coating. Suitable methods include, for example, vapor phase deposition (e.g., vacuum evaporation, sputter coating, and chemical vapor deposition) solution coating or dispersion coating (e.g., (lip coating, spray coating, spin coating, pour coating (i.e., pouring a liquid over a surface and allowing the liquid to flow over the whisker layer, followed by solvent removal)), immersion coating (i.e., immersing the whisker layer in a solution for a time sufficient to allow the layer to adsorb molecules from the solution, or colloidals or other particles from a dispersion), electroplating and electrodeless plating. More preferably, the conformal coating is deposited by vapor phase deposition methods, such as, for example, ion sputter deposition, cathodic arc deposition, vapor condensation, vacuum sublimation, physical vapor transport, chemical vapor transport, and metalorganic chemical vapor deposition. Preferably, the conformal coating material is a catalytic metal or metal alloy.

For the deposition of a patterned conformal coating, the deposition techniques are modified as is known in the art to produce such discontinuous coatings. Known modifications include, for example, use of masks, shutters, directed ion beams, and deposition source beams.

The electrode particles can be embedded in the partially filled membrane by applying heat and mechanical pressure and subsequently removing the original substrate supporting the particles. Any suitable source of pressure may be employed. A hydraulic press is preferably employed. Alternately, pressure may be applied by one or a series of nip rollers. This process is also adaptable to a continuous process, using either a flat bed press in a repeating operation or rollers in a continuing operation. Shims, spacers, and other intermediate mechanical devices may be employed. The electrode particles are preferably supported on a substrate which is applied to the membrane surface, such that the particles contact the membrane surface. The substrate is removed after pressing, leaving the electrode particles embedded in the membrane. Alternately, the electrode particles may be applied directly to the membrane surface, free of any substrate and without inclusion of any additional ionomer, and then pressed into the surface. In one embodiment, a partially filled membrane disk may be placed between two sheets of polyimide-supported nanostructured films of nanostructured elements which are placed against the partially filled membrane. Additional layers of uncoated polyimide and PTFE sheets are further layered on either side of the sandwich for uniform distribution of pressure, and finally a pair of stainless steel shims is placed outside of this assembly.

The pressure, temperature and duration of pressing may be any combination sufficient to exclude void volume from the membrane and embed the electrode particles in the membrane. The optimum conditions depend on the properties of the porous membrane. Preferably, a pressure of between 0.05 and 10 tons/cm$^2$ is used and more preferably a pressure of between 0.1 and 1.0 ton/cm$^2$. Most preferably, a pressure of between 0.10 and 0.20 ton/cm$^2$ is used. Preferably the press temperature is between 20° C. and 300° C., and most preferably between 80° C. and 250° C. The pressing time is preferably greater than one second and most preferably about one minute. After loading into the press, the MEA components may be allowed to equilibrate to the press temperature, at low or no pressure, prior to pressing. Alternately, the MEA components may be preheated in an oven or other apparatus adapted for the purpose. Preferably the MEA components are preheated for 1–10 minutes before pressing. The MEA may be cooled before or after removal from the press. The platens of the press may be water cooled or cooled by any other suitable means. Preferably, the MEA is cooled for 1–10 minutes while still under pressure in the press.

Figure 4:
FIG. 4 is a scanning electron micrograph taken at 1,000× magnification of a cross-section of an MEA of the present invention.

FIG. 4 is an SEM micrograph at 1000× of a cross-section of an MEA made by the method of the present invention.

In one embodiment, p-STSI is used as the electrolyte. In the resulting MEA, the porous structure of the composite membrane is apparently obliterated. The ion conducting membrane portion of the resulting MEA appears to be a homogenous combination of the membrane material and the electrolyte. The membrane loses its original porous structure and, in particular, has no remaining membrane-crossing pores. In this embodiment, any method may be used to partially fill the membrane, as described above. Any pressing conditions, described above, may be used. Any porous membrane may be used, however, polypropylene membranes and TIPS membranes are preferred and polypropylene TIPS membranes are most preferred.

This invention is useful in electrochemical devices such as fuel cells, electrolyzers, batteries, or gas, vapor or liquid sensors, using membrane electrodes optimized for the immediate purpose.

Objects and advantages of this invention are further illustrated by the following examples, but the particular materials and amounts thereof recited in these examples, as well as other conditions and details, should not be construed to unduly limit this invention.

EXAMPLES

Examples 1–19, below, demonstrate partial filling of various porous polymer membranes with various ion conducting electrolytes by several different methods. Examples 20–25, following, demonstrate partial filling of the membranes followed by pressing of the partially filled membranes with electrode particles.

Materials Used in the Examples

These porous membranes are used in the following examples:

TIPS™ membrane A is a polypropylene TIPS™ (Thermally Induced Phase Separation media), having 4.3 sec/50 cc Gurley, 0.84 micrometer (bubble point) pore size, about 70% void and 3.5 mil (89 microns) thickness. The membrane was prepared as follows: Polypropylene resin (DS 5D45, Shell Chemicals Co., Houston, Tex.) having a melt flow index of 0.65 dg/min. (ASTM D1238, Condition I), was fed into the hopper of a 40 mm twin-screw extruder (Berstorff Corp., Charlotte, N.C.). Amoco White Mineral Oil #31 (AMOCO, Chicago, Ill.) having a viscosity of 60 centistokes (ASTM D445 at 40° C.), was introduced into the extruder through an injection port at a rate to provide a composition of 31% by weight of polymer and 69% by weight mineral oil. The composition also contained 0.24% by weight dibenzylidene sorbital (Millad™ 3905, Milliken Chemical Corp., Spartanburg, N.C.) as a nucleating agent. The overall feed rate was 16.80 kg/hr. The polymer was heated to 266° C. in the extruder to melt it and, after mixing with oil, the temperature was maintained at 166° C. during extrusion. The melt was extruded through a 38.1 cm-side coat hanger slit die and cast onto a casting wheel maintained at 66° C. The cast film was extracted with dichlorotrifluoroethane ($CHCl_2CF_3$, available as Vertrel™ 423, DuPont Chemical Co., Wilmington, Del.) to remove mineral oil, then oriented 2.1 to 1 in the machine direction at 88° C. and 2.8 to 1 in the cross-direction at 140° C.

TIPS™ membrane B is a polypropylene TIPS™, having 68 secs/50 cc Gurley, 0.1 micrometer pore size, 58% void and 29 micrometers (1.13 mil) thickness. The membrane was prepared as follows: Polypropylene resin (DS 5D45, Shell Chemicals Co., Houston, Tex.) having a melt flow index of 0.65 dg/min (ASTMD1238, Condition I), was fed into the hopper of a 40 mm twin-screw extruder (Berstorff Corp., Charlotte, N.C.). Amoco White Mineral Oil #31 (AMOCO, Chicago, Ill.) having a viscosity of 60 centistokes (ASTM D445 at 40° C.), was introduced into the extruder through an injection port at a rate to provide a composition of 55% by weight of the polymer and 45% by weight mineral oil. The composition also contained 0.28% dibenzylidine sorbital (Millad™ 3905, Milliken Chemical Corp., Spartanburg, N.C.) as a nucleating agent. The overall feed rate was 11.35 kg/hr. The polymer was heated to 271° C. in the extruder to melt and, after mixing with oil, the temperature was maintained at 177° C. during the extrusion. The melt was extruded through a 38.1 cm-wide coat hanger slit die and cast onto a casting wheel maintained at 60° C. The cast film was extracted with dichlorotrifluoroethane ($CHCl_2CF_3$, available as Vertrel™ 423, DuPont Chemical Co., Wilmington, Del.) to remove mineral oil, then oriented 3.25 to 1 in the machine direction at 90° C. and 1.5 to 1 in the cross-direction at 138° C.

TIPS™ membrane C is a polyvinylidenedifluoride TIPS™, having 366 secs/50 cc Gurley number, 0.07 micrometer pore size, 44% void volume and 69 micrometer (2.7 mil) thickness. The membrane was prepared as follows: Solef™ 1010 polyvinylidenedifluoride (PVDF) resin (Solvay America Inc., Houston, Tex.) was fed into the hopper of a 40 mm twin-screw extruder (Berstorff Corp., Charlotte, N.C.). Dibutyl phthalate (Aldrich Chemical Co., Inc., Milwaukee, Wis.) was introduced into the extruder through an injection port at a rate to provide a composition of 60% by weight of the polymer and 40% by weight dibutyl phthalate. The overall feed rate was 14.8 kg/hr. The melt was extruded at 204° C. through a 30.5 cm-wide coat hanger slit die and quenched in a water bath maintained at 28° C. The cast film was extracted with 1,1,1 trichloroethane (Aldrich) to remove dibutyl phthalate, then oriented 1.3 to 1 in the machine direction at 32° C. and 1.5 to 1 in the cross-direction at 121° C.

The fourth membrane, Poreflon™, is an expanded polytetrafluoroethylene (PTFE) produced by Sumitomo Electric Industries, Inc., Tokyo, Japan, which has a Gurley number of 17.5±0.5 seconds/100 cc.

In the preceding, Gurley number refers to a measure of the resistance to gas flow of a membrane, expressed as the time necessary for a given volume of gas to pass through a standard area of the membrane under standard conditions, as specified in ASTM D726-58, Method A. Gurley number is the time in seconds for 100 cc of air, or another specified volume, to pass through 6.35 $cm^2$ (one square inch) of a film at a pressure of 124 mm of water. The film sample is clamped between cylindrical rings, the uppermost of which contains a piston and the specified volume of air. When released, the piston applies pressure, under its own weight, to the air in the upper cylinder and the time taken for the specified volume of air to pass through the membrane is measured.

In the preceding, pore size refers to a measure of size of the largest pore in a membrane as specified in ASTM F-316-80. A liquid is used to fill the pores of the film. Air pressure is applied until air flows through the largest passageways in the film and appears as bubbles. The pressure at the point that bubbles appear is related to the size of the largest pores and the surface tension of the test liquid. Using ethanol as a test liquid, the bubble point in micrometers is equal to $1.34 \times 10^{-3}$ divided by the pressure in Pascals (Pa) at which bubbles appear.

These polymer electrolytes are used in the following examples:

Nafion™ 1100 solution: a solution of 1100 equivalent weight perfluorinated ion-exchange polymer having a $SO_3^-$ anion groups attached, produced by DuPont and available from ElectroChem, Inc., Woburn, Mass., and Aldrich. Solution of 5 wt % in a mixture of lower aliphatic alcohols and water (15–20% water).

p-STSI: An ion conductive material derived from free radical polymerization of styrenyl trifluoromethyl sulfonylimide (STSI); styrenyl-$SO_2N^-$ ($SO_2CF_3$).

Examples 1 and 2

Examples 1 and 2 illustrate partial filling of the porous membranes with electrolyte using a multiple dipping and drying process. In this approach the porous membrane was immersed in low concentration electrolyte solution for short times, dried in an air oven, and the process repeated multiple times, with measurements of the mass loading increase in between.

Figure 1:
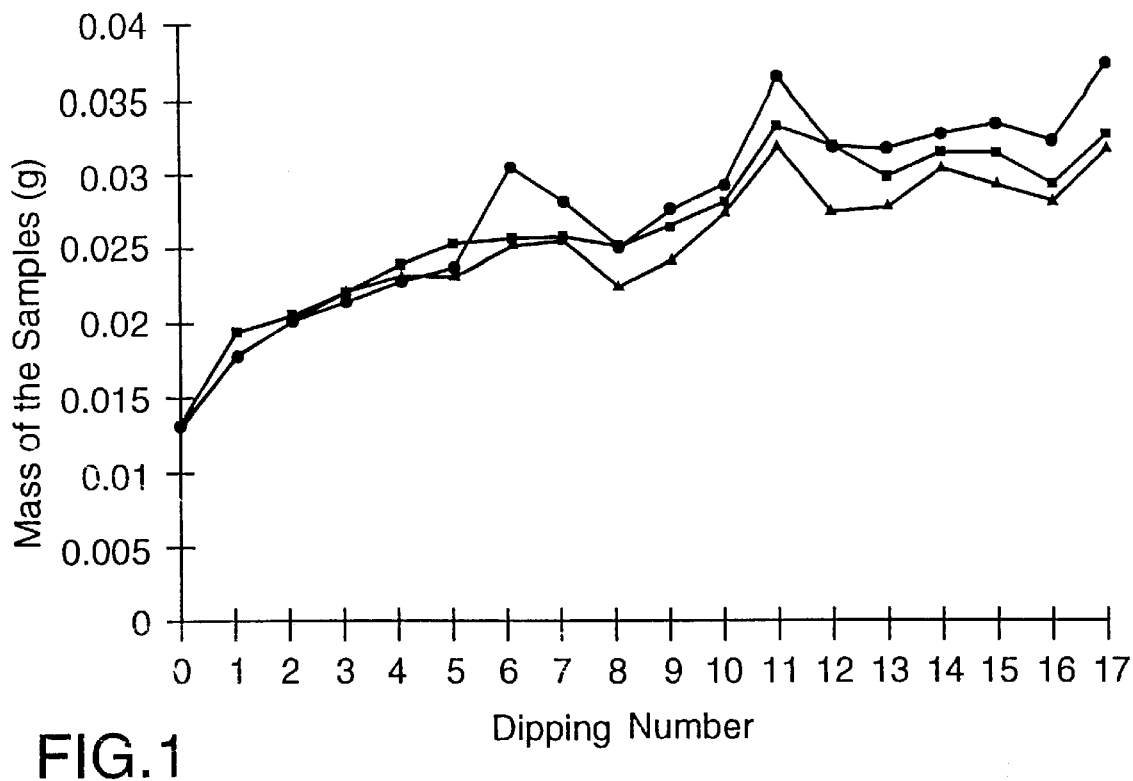
FIG. 1 is a graph of the average mass of three membrane samples after each of repeated steps of dipping in electrolyte solution and drying, according to the present invention.

In Example 1, three sample discs of the TIPS membrane B, 3.81 cm in diameter, were immersed in 5 wt % Nafion 1100 solution, removed, dried and weighed and the change in mass of each sample disc recorded. This procedure was repeated a total of 16 times. The duration of the immersion was varied, from as much as 20 minutes to as little as 2 minutes. Drying was accomplished in an air oven at about 50° C. The drying time was also varied, usually being between 15 and 20 minutes, but being as long as 2 hours in one case. Fresh solution was used after the sixth and eleventh dippings. After removal from the solution, the excess was allowed to drip off the discs before drying. A summary of the samples' masses after each such dip and dry procedure is shown in FIG. 1. After the $15^{th}$ dipping and drying, a wet cloth was used to further clean away any excess solution and the samples were weighed again (data point 16 in FIG. 1). Surface accumulation, which appears as a glossy coating, was absent after the wiping. The measurements indicate that the mass increases for all three samples were similar, increasing on average monotonically with dip number, more rapidly at first and then leveling off. The length of soaking time does not appear to be a significant parameter and the use of fresh solutions does not appear to have a significant effect. Finally, the mass increase does not appear to be due to accumulation on the surface, since wiping caused a negligible decrease in weight relative to the overall increase in weight.

The average overall mass increase for the 16 dip/dry cycles is about 20 mg, or 1.75 $mg/cm^2$, or 0.61 $g/cm^3$. The density of the Nafion 1100 electrolyte is approximately 2 $g/cm^3$, based on the density of Nafion 117, (1.97 $g/cm^3$) which is the polymeric electrolyte material of Nafion 1100 out of solution. The density increase of 0.61 $g/cm^3$ corresponds to filling about 30% of the volume of the membrane. Hence, the original void volume of the membrane, 58%, was approximately half filled by the multiple dipping/drying procedure.

This approach is readily adaptable to a continuous web filling process, wherein the membrane passes over a series of rollers in a serpentine fashion, passing into and out of a tank of electrolyte solution, with drying stations in between. The web would alternately be immersed in the electrolyte solution, pass out through drying stations (e.g. forced air or heat lamps), pass into the solution again and so on a desired number of times.

Figure 2:
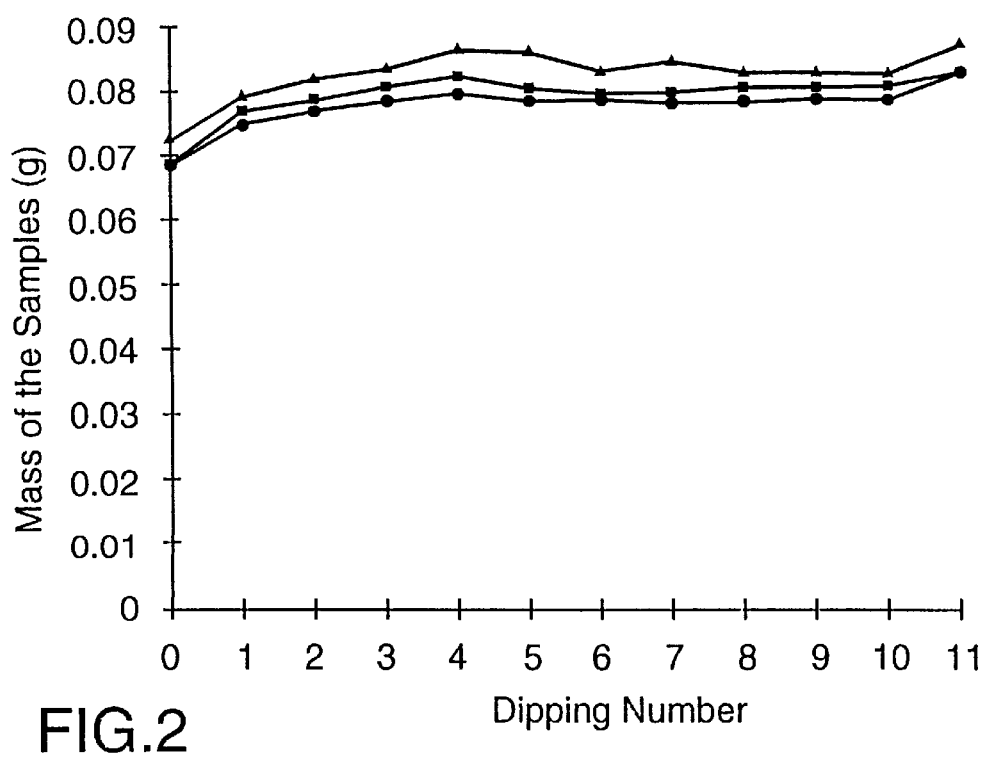
FIG. 2 is a graph of the average mass of three membrane samples after each of repeated steps of dipping in electrolyte solution and drying, according to the present invention.

In Example 2, the multiple dipping and drying procedure of Example 1 was repeated with three sample discs of the TIPS membrane C medium. The number of cycles was eleven. The immersion times varied from 4 minutes to 20 minutes and drying times from 18 minutes to 90 minutes. FIG. 2 summarizes the mass changes after each cycle. Again, the measurements indicate that the mass increases for all three samples were similar, that the length of soaking time does not appear to be a significant parameter and that the use of fresh solutions does not appear to have a significant effect. The mass increase is similar for all three samples and appears to level off after the $4^{th}$ cycle. The average overall mass increase is about 12 mg, or 1 $mg/cm^2$, or 0.15 $g/cm^3$. The TIPS membrane C medium has a smaller pore size and void volume (44%) than the TIPS membrane B medium which may account for the larger increase in density of the latter medium in Ex. 1. The maximum possible density increase is calculated to be 0.88 $g/cm^3$ of Nafion in the TIPS membrane C medium. The density increase of 0.15 $g/cm^3$ corresponds to filling about 7.5% of the volume of the membrane. Approximately a sixth of the original void volume of the membrane, 44%, was filled by the multiple dipping/drying procedure.

Examples 3–5

Examples 3, 4 and 5 illustrate partial filling of the porous membranes with electrolyte using a long soak method. In this approach, the porous membrane was immersed in the electrolyte solution for prolonged periods exceeding 20 minutes, then dried in an air oven.

In Example 3, two 3.15 cm diameter discs of TIPS membrane B were filled by soaking in 5 wt % Nafion solution for 30 minutes, then dried in an air oven at 50° C. for 50 minutes. The density increases were 0.31 $g/cm^3$ and 0.26 $g/cm^3$ respectively, averaging 0.29 $g/cm^3$.

In Example 4, a 3.81 cm diameter disc of TIPS membrane B was soaked for 5 hours in a 5 wt % solution. The container was not covered, so that the concentration could increase with time. After drying in an air oven for 45 minutes at about 50° C., the density increase was 0.44 $g/cm^3$.

In Example 5, two, 2.5 cm diameter discs of TIPS membrane A were soaked in 20 wt % p-STSI in DI water for 20 minutes. The excess was allowed to drain off and the discs were dried overnight. For both samples, the density increase was 0.16 $g/cm^3$.

Examples 6–12

Examples 6–12 illustrate partial filling of the porous membranes with electrolyte by use of a vacuum procedure. In this approach a small vacuum is applied to the underside of the porous membrane supported on a filter flask support, to force various electrolyte concentrations through the membrane.

In Examples 6–8 portions of the 5 wt % Nafion solution were dried down to prepare 10 and 20 wt % solutions. For each solution, single discs of TIPS membrane A, each 3.81 cm diameter, were placed over the holes in the flat bottom of a Coors D37 ceramic filter funnel inserted in the top of a 250 ml vacuum flask, connected via a rubber hose to a Venturi air device, Varian model 952-5096 (sold by Varian, Lexington, Mass.) to provide suction. Then 0.5 ml of solution was spread over the top of the membrane and vacuum was applied to pull solution through the membrane. For the most viscous solution, not all solution passed through but remained on the surface of the membrane. The samples were dried for 35 minutes at about 50° C. and weighed. The increase in mass due to electrolyte uptake was observed to increase monotonically with solution concentration from 0.20 g/cm³ at 5 wt % to 0.36 g/cm³ at 10 wt % to 0.71 g/cm³ at 20 wt %. Since any excess left on the surface was not removed for the 20 wt % sample, part of the density increase is due to a dried film left covering the surface.

In Example 9, the TIPS membrane B was filled with Nafion 5 wt % solution in the same apparatus described in Ex. 6. Sample diameters were 3.15 cm. 15 drops of solution were added to the first discs. The solution was allowed to wet the TIPS for 2 minutes, then vacuum was applied for 10 seconds. For the second disc, 17 drops were applied for 3 minutes before vacuum was applied for 50 seconds. After drying the density increases were measured to be 0.26 g/cm³ and 0.35 g/cm³ respectively.

In Example 10, two 3.81 cm diameter discs of TIPS membrane C were vacuum loaded with 5 wt % Nafion solution. 15 drops were applied to each surface, allowed to wet for one minute, then vacuum applied for 17 seconds in one case and 50 seconds in the second sample. The samples were dried at 50° C. for 25 minutes. The density increases were 0.06 g/cm³ and 0.054 g/cm³ respectively.

In Example 11, three discs, each 3.51 cm diameter, of the TIPS membrane A were partially filled with Nafion using 5 wt % solutions and the vacuum pull through method of Ex. 6. For the first disc, a total of 1 ml of solution was passed through, in two 15 drop lots. For the second 2 ml of solution was passed through and for the third, 3 ml was used. After drying the respective density increases were 0.298 g/cm³, 0.301 g/cm³ and 0.303 g/cm³. Example 11 demonstrates that the increase in density observed using the vacuum method, and hence the amount of ionomer adsorbed, becomes independent of the total volume of electrolyte solution passed through the membrane.

In Example 12, two 2.5 cm discs of TIPS membrane A were filled with p-STSI from a 20 wt % solution using the same procedure as in Example 6. Six drops of solution were added to the surface and vacuum applied for 2 minutes. After drying, the change in density was 0.17 g/cm³ and 0.13 g/cm³, averaging 0.15 g/cm³.

Examples 13–19

Examples 13–19 illustrate partial filling of the porous membranes with electrolyte using positive pressure provided by a hydraulic press. In the hydraulic press approach, a room temperature mechanical press is used to hydraulically force high concentration (viscous) electrolyte solutions through the porous membrane.

In the following Examples, two pieces of 100 micrometer thick polyethylene terephthalate (PET) film were prepared as masks by cutting 3.7 cm diameter holes in their centers. The porous membrane material was sandwiched between the two PET masks. This sandwich was further sandwiched between two sheets of 0.025 cm thick PTFE, after applying the electrolyte solution into the volume (about 0.1 ml) defined by the holes in the PET mask. This sandwich was placed between stainless steel shim stock. The entire assembly was placed between the platens of a hydraulic press (manufactured by Fred S. Carver, Inc., Wabash, Ind.) and a force of 3.2 tons applied for 3–5 minutes at room temperature. After pressing, excess solution was wiped off the surface of the membrane and the latter dried in an air oven at about 48° C. for 12 minutes. A disc of measured diameter was die cut from the center of the partially filled membrane sample and its mass loading of electrolyte gravimetrically determined.

In Example 13, two samples of TIPS membrane B were filled with Nafion using a 5 wt % solution and the procedure described above and 3.15 cm diameter discs were die cut from the resulting membrane. The density increases after drying were 0.11 g/cm³ and 0.076 g/cm³, averaging 0.093 g/cm³.

In Example 14, two samples of the TIPS membrane C were filled with Nafion using a 5 wt % solution and the same procedure as in Ex. 13 and 3.81 cm diameter discs were die cut from the resulting membrane. The density increases after drying were 0.037 g/cm³ and 0.045 g/cm³, averaging 0.041 g/cm³.

In Example 15, the hydraulic press method described in Example 13 was used to fill 3 samples of TIPS membrane B with p-STSI from 20 wt % solutions in 70/30 methanol and water. Three to four drops of solution were used for each side, pressed for 3 minutes at 3 tons, then dried 20 minutes at about 50° C. after wiping the excess electrolyte off the surface. Three 3.25 cm diameter discs were cut from the resulting membrane;. The density increases were 0.049 g/cm³, 0.014 g/cm³ and 0.060 g/cm³ for an average increase of 0.041 g/cm³.

In Example 16, the procedure of Example 15 was repeated with two more samples, using 4 drops on each side from a 20 wt % solution of p-STSI in water only. The excess was wiped off and the samples dried at 55–60° C. for 23 minutes, and 3.81 cm diameter disks were cut from the resulting membranes. The density increase were 0.028 g/cm³ and 0.19 g/cm³ for an average increase of 0.11 g/cm³.

In Examples 17 and 18, the procedures used in Examples 15 and 16 were repeated using, three TIPS membrane C sample discs with 20 wt % solution of p-STSI in 70/30 MeOH/H2O, for 17 and two sample discs with p-STSI in pure water, for 18. The density increases of the first three discs were 0.098 g/cm³, 0.091 g/cm³ and 0.149 g/cm³ averaging 0.113 g/cm³. The increases of the next two were 0.25 g/cm³ and 0.088 g/cm³ averaging 0.17 g/cm³.

In Example 19, a 3.85 cm diameter disc of 50 micrometer thick Poreflon™ was filled using the procedure of Ex. 13. The porosity of the as received Poreflon was characterized by Gurley measurements and found to be 17.5±0.5 seconds/100 cc. Fifteen drops of a 4 wt % solution of Nafion 1100 was added to one side of the membrane (in the volume defined by the 100 micrometer thick PET mask aperture) and pressed at 2 tons for 4 minutes at room temperature. The excess Nafion was wiped off and the membrane dried at 49° C. for 15 minutes. The density increase was 0.22 g/cm³. The Gurley number of the filled sample was measured to be over 900 seconds/4 cc, corresponding to 22,500 seconds /100 cc.

Summary of Density Increase Data

Examples 1–19 demonstrate the density increase due to electrolyte incorporation by the various porous membranes for four filling procedures. Table I, below, summarizes the average results for Examples (including Example 20, below) that used Nafion electrolyte with four different porous membranes and four different methods. Table II, below, summarizes the average results for Examples (including Example 24, below) that used pSTSI electrolyte with three different porous membranes and three different methods.

TABLE I

Summary of density increases in g/cm³ of four different porous membranes filled from Nafion ™ solution using four different procedures

| Filling Method | TIPS membrane A | TIPS membrane B | TIPS membrane C | Poreflon ™ |
|---|---|---|---|---|
| Multi-Dip and Dry | | 0.61 (Ex. 1) | 0.15 (Ex. 2) | |
| Long Soak | | 0.29 (Ex. 3) | | |
| | | 0.44 (Ex. 4) | | |
| Vacuum | 0.20 (Ex. 6) | 0.31 (Ex. 9) | 0.057 (Ex. 10) | |
| | 0.36 (Ex. 7) | | | |
| | 0.71 (Ex. 8) | | | |
| | 0.301 (Ex. 11) | | | |
| Hydraulic Press | 0.35 (Ex. 20) | 0.093 (Ex. 13) | 0.041 (Ex. 14) | 0.22 (Ex. 19) |

TABLE II

Summary of density increases in g/cm³ of three different porous membranes filled from p-STSI solution using three different procedures

| Filling Method | TIPS membrane A | TIPS membrane B | TIPS membrane C |
|---|---|---|---|
| Long Soak | 0.16 (Ex. 5) | | |
| Vacuum | 0.15 (Ex. 12) | | |
| Hydraulic press | 0.15 (Ex. 24) | 0.041 (Ex. 15) | 0.113 (Ex. 17) |
| | | 0.109 (Ex. 16) | 0.17 (Ex. 18) |

Examples 20–25

Examples 20–25, following, demonstrate partial filling of the membranes followed by pressing of the partially filled membranes with electrode particles to form membrane electrodes. The electrode particles used in Examples 20–25 are nanostructured catalyst particles consisting of catalyst materials, e.g. Pt, conformally coated onto nanometer sized whisker-like supports, as described above and in U.S. Pat. No. 5,338,4.30 and other patents referenced therein, incorporated herein by reference. The whiskers used herein were produced by vacuum annealing thin films (about 1000–1500 Angstroms) of perylene red (PR149, described above) previously vacuum coated onto substrates such as polyimide. The whisker-like supports, with lengths of about 1–2 micrometers, were grown with uniform cross-sectional dimensions of about 30–60 nanometers, end-oriented on a substrate to form a dense film of closely spaced supports (about 30–40 per square micrometer) for transfer into the surface of a polymer electrolyte to form the catalyst electrode, as described below. The nanostructured catalyst electrode has a very high surface area which is readily accessible to fuel and oxidant gases.

Example 20

In Example 20, two 7.6×7.6 cm square pieces of 100 micrometer thick PET film were prepared as masks by cutting 3.7 cm diameter holes in their centers. A 7.6 cm×7.6 cm piece of the TIPS membrane A porous membrane material was sandwiched between the two PET masks. This sandwich was further sandwiched between two sheets of 0.025 cm thick Teflon, after applying 6 to 7 drops of a 25 wt % Nafion 1100 solution into the volume (about 0.1 ml) defined by the PET mask holes. The 25 wt % Nafion solution was obtained from the purchased 5 wt % solution by solvent evaporation. This sandwich was placed between stainless steel shim stock. The entire assembly was placed between the platens of a Carver press and a force of 3.2 tons applied for 5.0 minutes at room temperature. Assuming about 30 drops/ml, the 6–7 drops should represent an excess by about a factor of two over what is needed to fill the 70% void volume of the membrane, assuming that all of the volume was accessible. After pressing, excess Nafion solution was wiped off the surface of the membrane and the latter dried in an air oven at about 48 C. for 12 minutes. A 3.5 cm diameter disc was die cut from the center of the filled membrane and its mass loading of Nafion gravimetrically determined to be 2.88 mg/cm², or 0.32 g/cm³.

The Gurley number of the as-received TIPS membrane A was measured to be 8 secs/100 cc. In order to obtain the Gurley number of the filled membrane, a second sample of the TIPS membrane A was partially filled using the Carver press and 14% Nafion solution with the same procedure as described above. The Gurley number for this sample, without attached electrodes, was measured to be over 900 secs/3 cc, corresponding to 30,000 sec/100 cc.

Next, a three layer membrane electrode assembly, comprising an electrode layer, an ICM, and a second electrode layer, was formed by using heat and pressure to transfer nanostructured electrode particles from a polyimide substrates into both surfaces of the partially filled membrane. The filled membrane disc was placed between two sheets of polyimide-supported nanostructured films of nanostructured elements. These elements, which were PR149 whiskers coated with a mass equivalent layer thickness of first 3000 Angstroms of Ni and secondly, 1000 Angstroms of Pt, were placed against the partially filled membrane. Additional layers of uncoated polyimide and PTFE sheets were further layered on either side of the sandwich for uniform distribution of pressure, and finally a pair of stainless steel shims were placed outside of this assembly. The assembly was placed between the heated platens of a mechanical press (Carver 6" press) at low pressure, allowed to equilibrate to 99° C. for several minutes, pressed at 15.1 MPa (0.17 tons/cm²) for 90 seconds, left under pressure while the platens were water cooled for several minutes, then removed. The original polyimide substrates were then peeled away from the membrane. The transfer of catalyst particles was complete and very uniform.

FIG. 3 is a scanning electron micrograph taken at 2000× magnification of the surface of the as-received TIPS membrane A material used in Example 20, viewed from the top, showing the large degree of porosity.

FIG. 4 is a scanning electron micrograph taken at 1000× of a cross-section of the MEA, showing that the thickness of the membrane electrode assembly is now about 33 micrometers, having been reduced from the initial membrane thickness of about 89 micrometers.

Figure 5:
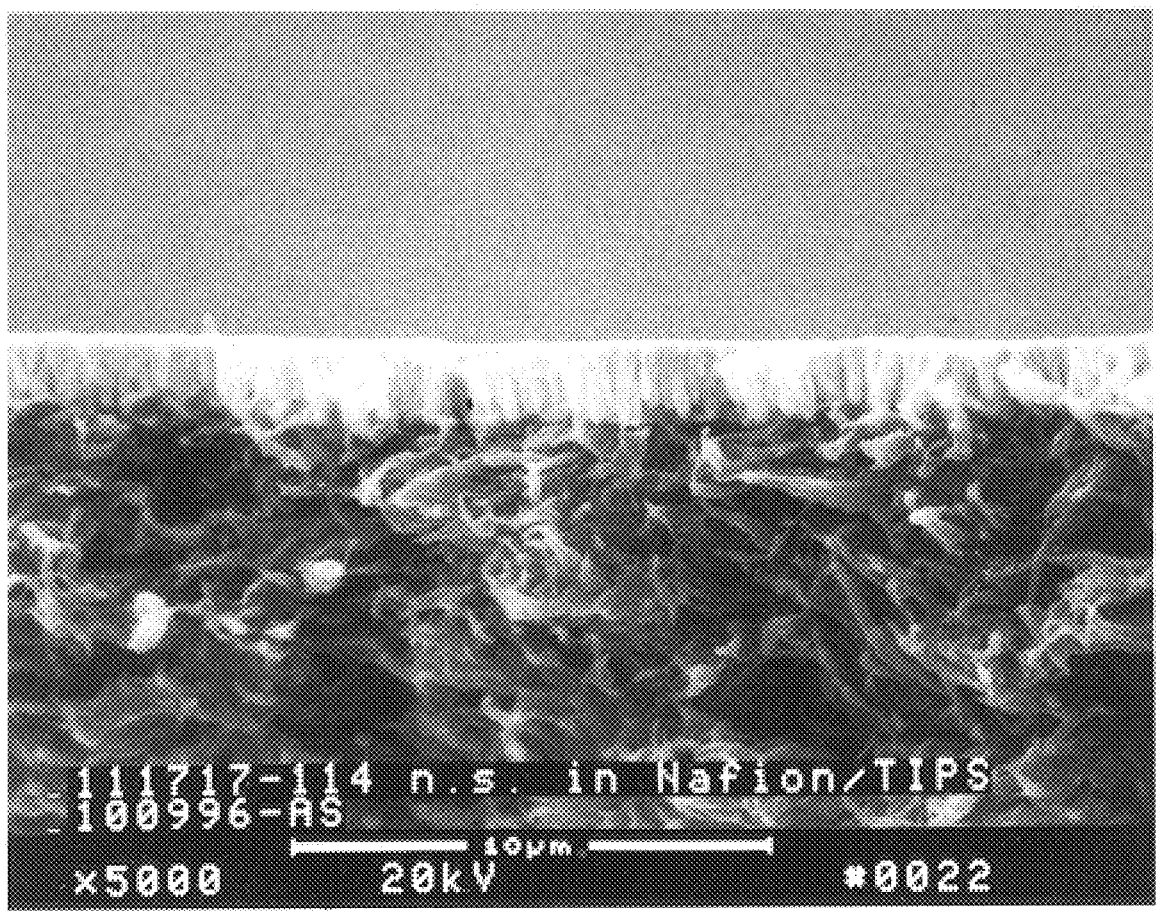
FIG. 5 is a scanning electron micrograph taken at 5,000× magnification of a cross-section of an MEA of the present invention.

FIG. 5 is a scanning electron micrograph taken at 5000× of one of the electrode sides showing the electrode particles embedded in the membrane. The fractured edge of the membrane shows some evidence of the fibril nature of the original polypropylene matrix.

Figure 6:
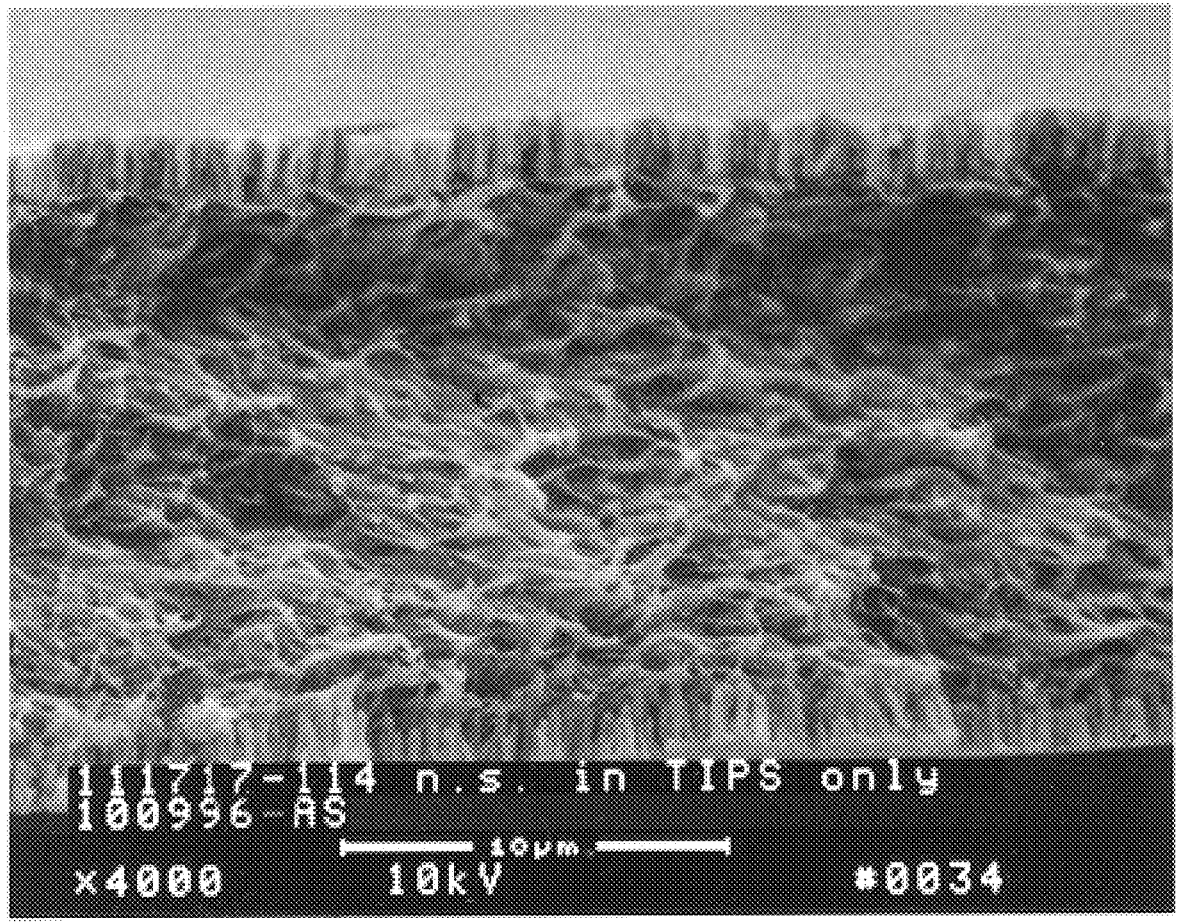
FIG. 6 is a scanning electron micrograph taken at 4,000× magnification of a cross-section of a comparative MEA omitting electrolyte.

For comparison., a portion of the membrane that was not filled with Nafion was impregnated with electrode particles. FIG. 6 is a scanning electron micrograph taken at 4000× showing that the thickness of this portion was reduced to about 15 micrometers, or about $\frac{1}{6}^{th}$ the original thickness. In contrast, the membrane was only compressed to about $\frac{1}{3}^{rd}$ the original thickness after the partial filling step.

Example 21

In Example 21, two 7.6×7.6 cm square pieces of 50 micrometer thick polyimide film were prepared as masks by cutting 2.23 cm×2.23 cm square holes (5 cm² in area) in their centers. A 7.6 cm×7.6 cm piece of the TIPS membrane A porous membrane material was sandwiched between the two polyimide masks. After application of 6 to 7 drops of a 14 wt % Nafion 1100 solution into the volume defined by the square holes, this sandwich was further sandwiched between two whole sheets of the polyimide and finally two sheets of 0.025 cm thick Teflon. This sandwich was placed between stainless steel shim stock and the entire assembly placed between the platens of a Carver press. A force of 3.2 tons was applied for 3 minutes at room temperature. After pressing, the outer polyimide layers were removed and excess Nafion solution was wiped off the surface of the TIPS membrane in the area defined by the square holes, the TIPS being left sandwiched between the initial polyimide masks. The assembly was dried in an air oven at about 48 C. for 25 minutes.

An MEA was formed using nanostructured films composed of electrode particles supported on a polyimide substrate. The nanostructured electrode particles used in Example 21 were supported on a polyimide substrate, as in Ex. 20, but were coated with 1000 Angstroms mass equivalent of Pt, rather than Ni and then Pt. Square pieces of the polyimide supported nanostructured films, 5 cm² in area, were placed in each square hole of the masks. The assembly was preheated to 210–215° C., pressed at 14.2 MPa (0.12 tons/cm²) for one minute, and cooled under pressure. The polyimide substrates supporting the whiskers were peeled away leaving the Pt coated nanostructure in the 5 cm² area of the filled membrane. SEM micrographs show the compressed 3-layer MEA to be 31 micrometers thick and demonstrate that the pressing process embedded the nanostructured electrode particles in the surface of the filled membrane.

To make a fuel cell from this MEA, each 5 cm² electrode area of the 3 layer MEA was covered with an equivalent sized square of a carbon-only ELAT™ material, available from Etek, Inc., Natick, Mass. as a fuel cell electrode backing material. The ELAT is a composite made of a woven carbon cloth and a carbon black/Teflon coating. The resulting five-layer cell was mounted in a fuel cell test fixture supplied by Fuel Cell Technologies, Inc., Albuquerque, N. Mex., which is made to accept the size and shape of the MEA. The five layer MEA was tested with $H_2$/oxygen gas flows applied to the respective electrodes using a fuel cell test station from Fuel Cell Technologies, Inc.

Figure 7:
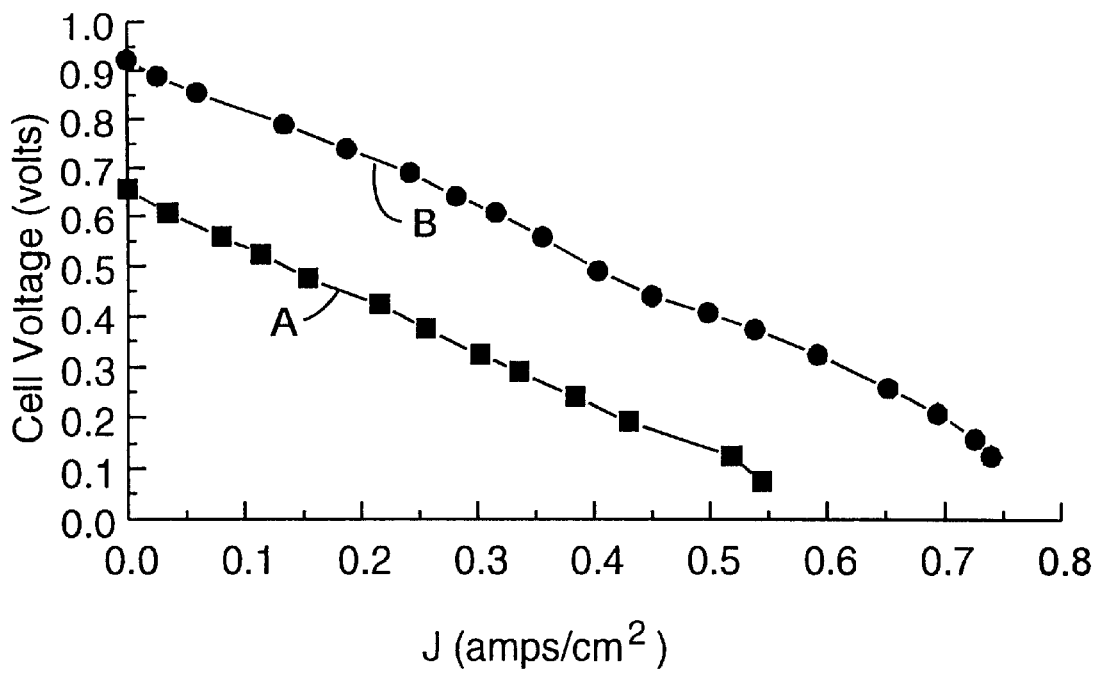
FIG. 7 is a graph of a polarization curve of voltage versus current density produced by two fuel cell assemblies of the present invention.

FIG. 7, curve A shows an initial polarization curve of voltage versus current density produced by the fuel cell assembly of this example under hydrogen and oxygen pressures of 63 kPa absolute (9 psig) and 327 kPa absolute (18 psig), respectively, a cell temperature of 40° C., and 200 sccm flow rates.

Example 22

In Example 22, a three layer MEA was prepared using the same TIPS membrane A membrane partially filled with Nafion, the same type of nanostructured electrodes and the same procedures as described in Example 21. However, prior to attaching nanostructured electrodes, an additional drop of 5 wt % Nafion solution was applied to each area of filled membrane exposed through the 5 cm² square holes of the polyimide masks, and dried at 40° C. for 15 minutes. Pt coated electrode particles were attached as in Ex. 21. In this instance, the Pt coated electrode particles are embedded into the thin surface layer of solution cast Nafion left on the surface of the filled membrane. Assuming 30 drops per ml, the dried thickness of the cast Nafion layer would be about 3 micrometers. The nanostructure electrode particles are about 1 to 2 micrometers long and about 30–60 nm wide.

The 3-layer MEA was tested as a fuel cell MEA with ELAT electrode backings, as described in Example 21. Curve B in FIG. 7 shows a polarization curve example under hydrogen/oxygen pressures of 170/205 kPa absolute (10/15 psig), a cell temperature of 70° C., and 200 sccm flow rates. After completing the tests, the MEA of this example was thoroughly dried. Its thickness was measured to be 25 micrometers, suggesting further compression of the membrane than in Example 21.

Examples 23–25

In Examples 23–25, MEAs were formed using p-STSI electrolyte in TIPS membrane A by two different loading processes and the MEAs were evaluated in a fuel cell. In both Examples, an unexpected change in the morphology of the membrane is demonstrated.

In Example 23, a 20 wt % solution of p-STSI in a 70/30 v/v mix of MeOH and water was prepared. A 2.5 cm diameter disc of the TIPS membrane A was placed over the holes iron the flat bottom of a Coors D37 ceramic filter funnel inserted in the top of a 250 ml vacuum flask, connected via a rubber hose to a Venturi air device to provide suction. Six drops of the solution were applied to the TIPS disc and air pressure applied to the Venturi device sufficient to pull the solution through the membrane, which process took about 8 seconds. After drying, the disk was about 75 micrometers thick at its center. FIG. 9 is a scanning electron micrograph taken at 1000× magnification of the top surface of the membrane. After being partially filled with p-STSI, illustrating a significant degree of open porosity still existing in the membrane.

Figure 10:
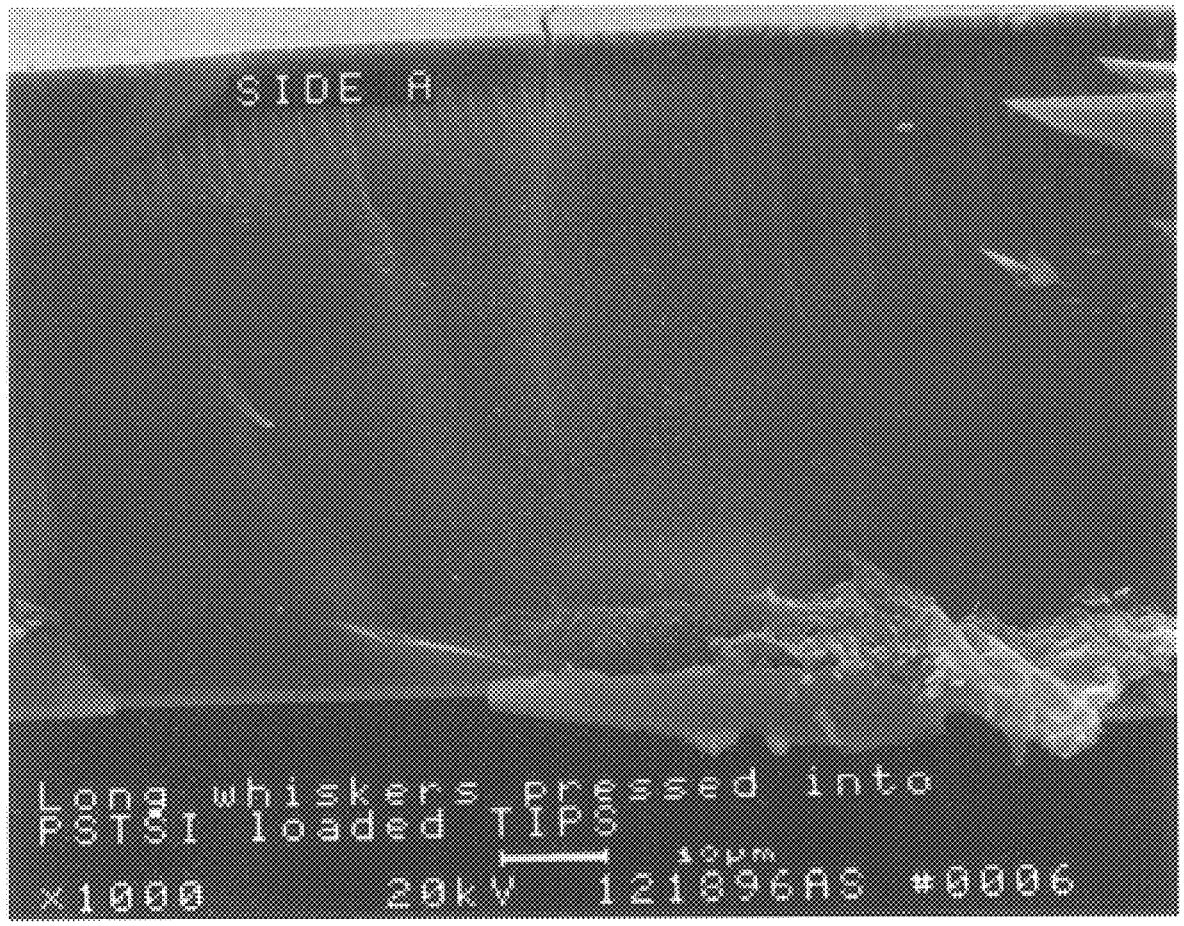
FIG. 10 is a scanning electron micrograph taken at 1,000× magnification of a cross-section of an MEA of the present invention.
Figure 11:
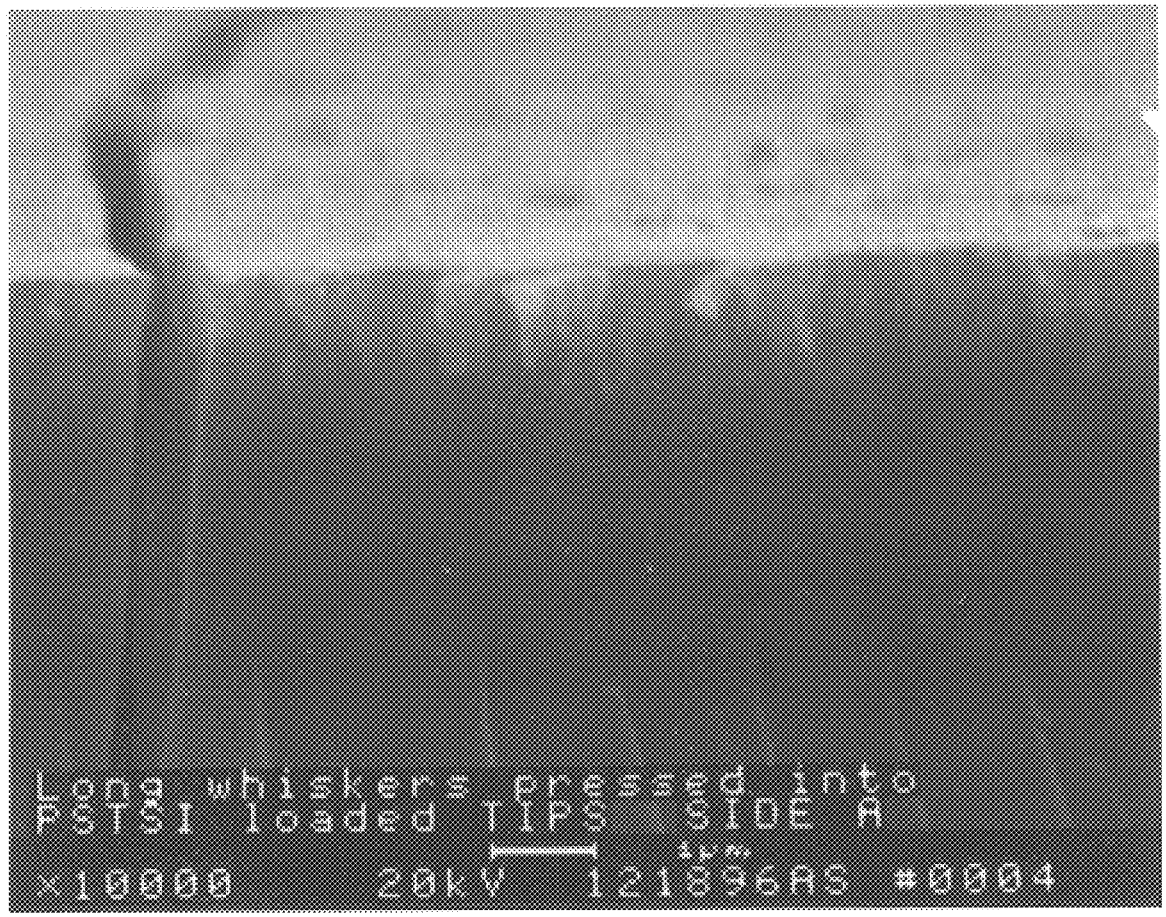
FIG. 11 is a scanning electron micrograph taken at 10,000× magnification of a cross-section of an MEA of the present invention.

Pt coated electrode particles similar to those described in Example 21 were pressed into the partially filled membrane using 18.9 MPa (0.16 tons/cm²) pressure at 110° C., by preheating for 1 minute, pressing for 1 minute and cooling under pressure for 4 minutes. FIG. 10 is a cross-sectional scanning electron micrograph taken 1000× magnification showing that the MEA thickness is reduced to 59 micrometers from the initial 89 micrometers. Surprisingly, the membrane now appears to be homogeneous and lacks any indication of the initial porosity. This uniformity is still seen at 10,000× magnification, in FIG. 11. FIG. 11 also shows the nanostructured electrode particles embedded in the surface of the membrane. The fact that the process of embedding the nanostructured electrode particles to form an MEA has so dramatically changed the morphology of the membrane interior was unexpected. Whereas the TIPS membranes coated from Nafion™ solution are observed under SEM to have the ionomer coated onto the fibrils of the porous membrane, it appears that the p-STSI has preferentially filled the pore voids as well as wetting the surface of the pore walls.

In Example 24, a 2.5 cm disc of TIPS membrane A membrane was partially filled with the same p-STSI solution as in Example 4, but using the hydraulic press method and PET masks as described in Ex. 11. Five drops of the solution were added to both sides of the 2.5 cm apertures in the PET masks to wet the exposed membrane, and pressed at room temperature with 3 tons for 3 minutes. The excess was wiped off the surface and the sample dried in an air oven at 50° C. for 30 minutes. The mass loading of p-STSI was measured to be 1.1 mg/cm² or 0.15 g/cm³. An MEA was formed by embedding the same Pt coated nanostructured film as in Ex.

Figure 12:
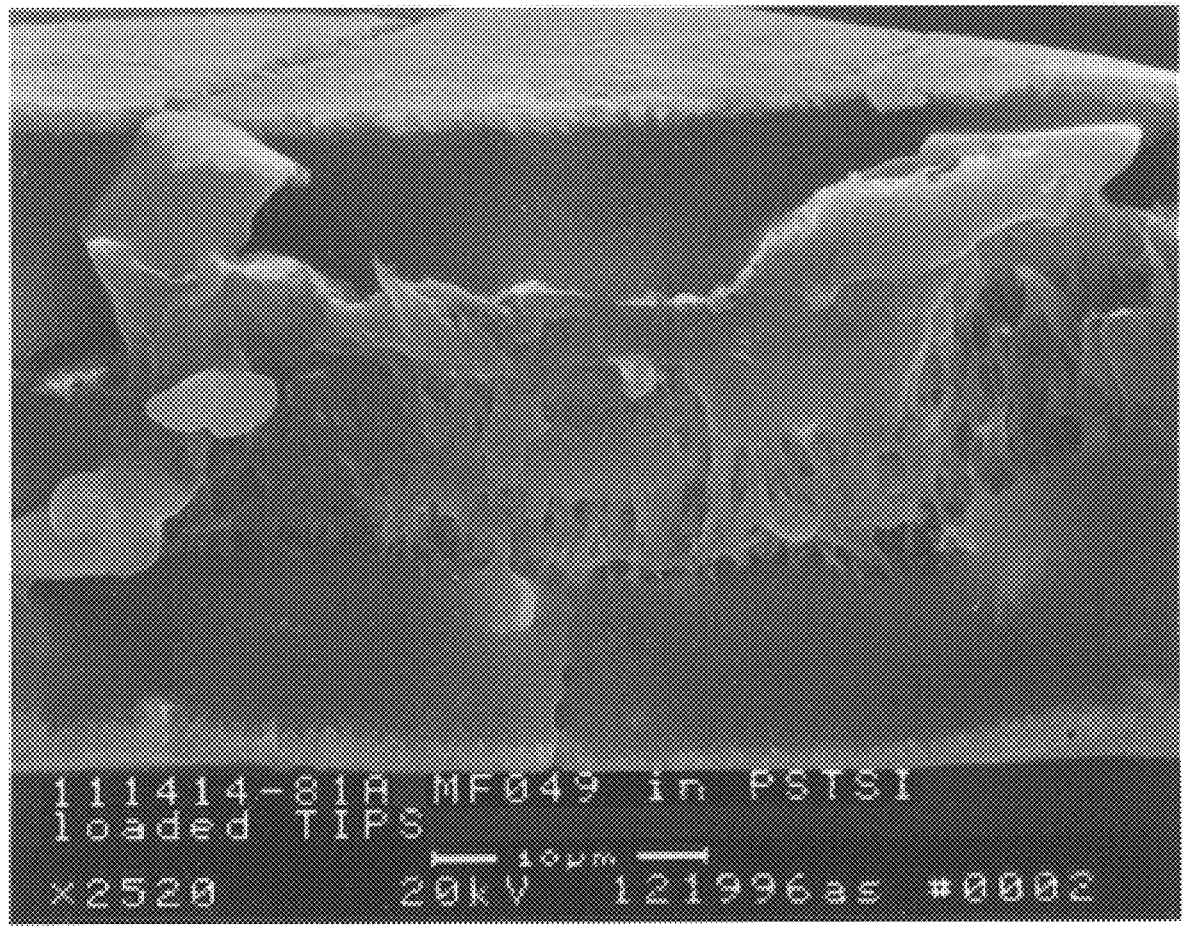
FIG. 12 is a scanning electron micrograph taken at 2,520× magnification of a cross-section of an MEA of the present invention.

23, using 84 MPa (0.71 tons/cm$^2$) pressure at the same pressing conditions used in Ex. 23. FIG. 12 is a cross-sectional scanning electron micrograph taken at showing the compressed MEA thickness to be 28 micrometers. FIG. 12 shows the internal membrane structure to be substantially homogeneous along its outer layers, as in FIGS. 10, but that some of the porous structure is still evident in the central portion, perhaps due to incomplete penetration of the electrolyte. However, no membrane-crossing pores are evident in FIG. 12.

Figure 8:
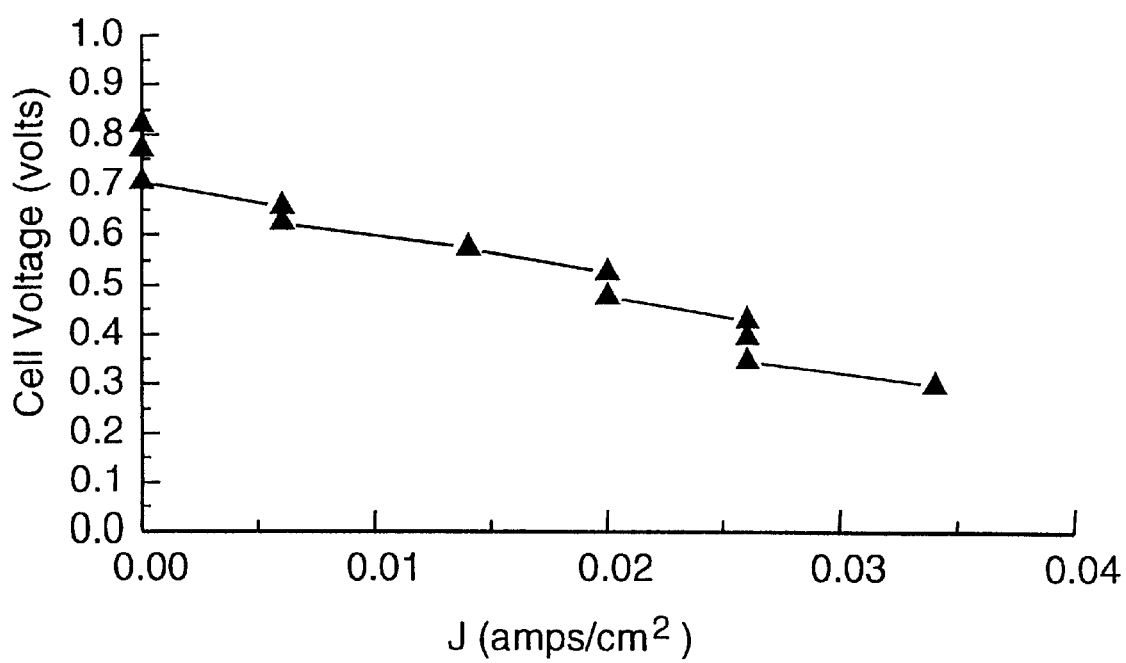
FIG. 8 is a graph of a polarization curve of voltage versus current density produced by a fuel cell assembly of the present invention.

In Example 25, the same filling procedure and similar electrode attachment procedures were followed as in Example 24. The electrode attachment was accomplished with 106.5 MPa (0.9 tons/cm$^2$) pressure at 230° F. for 1 minute with 5 minutes preheating and 5 minutes cooling under pressure. The fuel cell MEA sample was prepared in a square aperture between polyimide masks, the aperture being 5 cm$^2$ in area. The fuel cell MEA sample was tested as described in Ex. 20. FIG. 8 shows a polarization curve obtained at 50° C. and 5 psig H$_2$/O$_2$ pressures.

Various modifications and alterations of this invention will become apparent to those skilled in the art without departing from the scope and principles of this invention, and it should be understood that this invention is not to be unduly limited to the illustrative embodiments set forth hereinabove. All publications and patents are herein incorporated by reference to the same extent as if each individual publication or patent was specifically and individually indicated to be incorporated by reference.

We claim:

1. A method of making a membrane electrode assembly comprising the steps of:
    a) partially filling a porous membrane with an ion conducting electrolyte to form a partially filled membrane;
    b) providing electrode particles; and
    c) compressing together said partially filled membrane and electrode particles so as to remove void volume from said partially filled membrane and embed said electrode particles in said partially filled membrane.
2. The method according to claim 1, wherein said electrode particles are nanostructured elements.
3. The method according to claim 1, wherein said ion conducting electrolyte is polystyrenyl trifluoromethyl sulfonylimide (p-STSI).
4. The method according to claim 3, wherein said porous membrane is polypropylene.
5. The method according to claim 4, wherein said porous membrane is prepared by thermally-induced phase separation (TIPS).
6. The method according to claim 5, wherein the thickness of said membrane electrode assembly is less than or equal to about two thirds of the thickness of the porous membrane before partial filling.
7. The method according to claim 5, wherein the thickness of said membrane electrode assembly is less than or equal to about one third of the thickness of the porous membrane before partial filling.
8. The method according to claim 1, wherein the step of partially filling the porous membrane comprises at least one immersion step, comprising a) immersing the porous membrane in a solution of the ion conducting electrolyte and then b) drying the membrane.
9. The method according to claim 8 comprising at least two immersion steps.
10. The method according to claim 1, wherein the step of partially filling the porous membrane comprises mechanically compressing together the porous membrane and a solution of the ion conducting electrolyte.
11. The method according to claim 1, wherein the step of partially filling the porous membrane comprises forcing a solution of the ion conducting electrolyte into the porous membrane by air pressure differential.
12. An electrochemical device comprising the membrane electrode assembly made according to the method of claim 1.
13. A fuel cell comprising the membrane electrode assembly made according to the method of claim 1.
14. A membrane electrode assembly made according to the method of claim 1.

* * * * *